United States Patent [19]

Kato et al.

[11] Patent Number: 4,880,798
[45] Date of Patent: * Nov. 14, 1989

[54] CEPHALOSPORIN DERIVATIVES

[75] Inventors: Kazuo Kato, Mishima; Kimihiro Murakami; Hidenori Mochizuki, both of Gotenba; Ei Mochida, Toshima, all of Japan

[73] Assignee: Mochida Pharmaceutical Co., Ltd., Tokyo, Japan

[*] Notice: The portion of the term of this patent subsequent to Sep. 12, 2006 has been disclaimed.

[21] Appl. No.: 123,526

[22] Filed: Nov. 20, 1987

[30] Foreign Application Priority Data

| Nov. 25, 1986 | [JP] | Japan | 61-280020 |
| Nov. 25, 1986 | [JP] | Japan | 61-280021 |
| Jan. 26, 1987 | [JP] | Japan | 62-015459 |
| Jan. 26, 1987 | [JP] | Japan | 62-015460 |
| Jan. 26, 1987 | [JP] | Japan | 62-015461 |

[51] Int. Cl.$^4$ .................. C07D 501/36; A61K 31/545
[52] U.S. Cl. .................................... 514/206; 540/227; 540/222
[58] Field of Search ................. 540/227, 226; 514/206

[56] References Cited

U.S. PATENT DOCUMENTS

| 4,103,085 | 7/1978 | Naito et al. | 544/27 |
| 4,104,469 | 8/1978 | Naito et al. | 544/27 |
| 4,151,352 | 4/1979 | Naito et al. | 544/26 |
| 4,278,793 | 7/1981 | Durkheimer et al. | 544/27 |
| 4,316,024 | 2/1982 | Iimura et al. | 548/27 |
| 4,331,666 | 5/1982 | Nannini et al. | 424/246 |
| 4,436,912 | 3/1984 | Wheeler | 548/233 |
| 4,500,526 | 2/1985 | Imae et al. | 514/226 |
| 4,526,977 | 7/1985 | Commons et al. | 548/246 |
| 4,547,494 | 10/1985 | Oine et al. | 514/204 |
| 4,576,956 | 3/1986 | Makisumi | 514/380 |
| 4,587,333 | 5/1986 | Ono et al. | 544/21 |
| 4,594,417 | 6/1986 | Yang | 544/28 |
| 4,600,773 | 7/1986 | Engel | 544/30 |
| 4,604,457 | 8/1986 | Torii et al. | 540/223 |
| 4,609,654 | 9/1986 | Labeeuw et al. | 540/237 |
| 4,621,081 | 11/1986 | O'Callaghan et al. | 540/227 |

FOREIGN PATENT DOCUMENTS

| 75805 | 4/1983 | European Pat. Off. . |
| 150507 | 8/1985 | European Pat. Off. . |
| 2128498 | 12/1971 | Fed. Rep. of Germany . |
| 2456109 | 12/1980 | France . |
| 60-142987 | 7/1985 | Japan . |
| 61-126089 | 6/1986 | Japan . |
| 189245 | 1/1977 | New Zealand . |
| 203436 | 6/1980 | New Zealand . |
| 186968 | 4/1981 | New Zealand . |
| 188163 | 10/1981 | New Zealand . |
| 196642 | 7/1984 | New Zealand . |
| 202332 | 10/1985 | New Zealand . |
| 206704 | 4/1986 | New Zealand . |
| 86/05786 | 10/1986 | PCT Int'l Appl. . |
| 893428 | 4/1962 | United Kingdom . |
| 1399086 | 6/1975 | United Kingdom . |
| 2017702A | 10/1979 | United Kingdom . |
| 1576625 | 10/1980 | United Kingdom . |
| 1604971 | 12/1981 | United Kingdom . |
| 2104888A | 3/1983 | United Kingdom . |

OTHER PUBLICATIONS

J. Antibiotics 36; 532, 1983, T. Nakagome et al.
J. Antibiotics 37; 532, 1984, T. Kamiya et al.
J. Antibiotics 30; 1236, 1986, M. Arimoto et al.
J. Antibiotics 39; 1243, 1986, M. Arimoto et al.
Chem. Abstracts 102:113169e.
Dunn, J. Antimicrob Chemotheraph (1982) 10 Suppl. C, pp. 1–10.
Naito et al., "Cephalosporins III," 30 Journal of Antibiotics 705 (9/77), (Aug. 1983).
Alpegian et al., Cepholosporins VI, 36 Journal of Antibiotics pp. 1013–1019.
Chemical Abstracts, vol. 103, 1985, Abstract No. 37281p.
Chemical Abstracts, vol. 100, 1984, Abstract No. 22505d.
Chemical Abstracts, vol. 102, 1985, Abstract No. 6056u.
Chemical Abstracts, vol. 102, 1985, Abstract No. 24539z.

*Primary Examiner*—Nicholas S. Rizzo
*Attorney, Agent, or Firm*—Oliff & Berridge

[57] ABSTRACT

The present invention relates to novel cephalosporin derivatives, processes for preparing thereof, compositions for preventing and/or treating infectious diseases which comprise the novel cephalosporin derivatives as active components, and the intermediate compounds in the synthesis of cephalosporin derivatives and processes for producing thereof.

The present invention is based on the selection of groups containing a condensed heterocyclic ring, particularly a triazolopyrimidine ring, as substitutents at the 3-position of the cephem skeleton, and of groups containing a carboxyl and hydroxy substituted phenylmethyloxyimino moiety, particularly a (carboxy substituted catechol)methyloxyimino moiety, as substituents at the 7-position of the cephem skeleton.

The compounds of the present invention containing the aforementioned substituents have a strong antibacterial activity against Gram-negative bacteria and also against Gram-positive bacteria including methicillin-resistant *Staphylococcus aureus*. These compounds are extremely useful for the treatment of infectious diseases.

15 Claims, No Drawings

CEPHALOSPORIN DERIVATIVES

BACKGROUND OF THE INVENTION

The present invention relates to novel cephalosporin derivatives, intermediate compounds, processes for producing cephalosporin derivatives, processes for producing intermediate compounds and compositions containing cephalosporin derivatives for treating and/or preventing infectious diseases.

Developments of cephalosporin derivatives have been remarkable. Some cephalosporin derivatives have been developed which have excellent antibacterial activity against Gram-negative bacteria. However, the antibacterial activity of these cephalosporin derivatives is rather poor against Gram-positive bacteria. Several cephalosporin antibiotics have been used for the treatment of Gram-positive bacteria infections and the increase of Gram-positive bacteria resistant to cephalosporin antibiotics, for example, methicillin-resistant *Staphylococcus aureus* (MRSA), has become widely known year by year.

From the foregoing background, it has been desired to develop cephalosporin derivatives having a strong antibacterial activity against Gram-positive bacteria while retaining a sufficient antibacterial activity against Gram-negative bacteria.

SUMMARY OF THE INVENTION

An object of the present invention is to provide novel cephalosporin derivatives and salts, solvates and salts of solvates thereof.

Another object of the present invention is to provide processes for producing novel cephalosporin derivatives.

A further object of the present invention is to provide compositions for preventing and/or treating infectious diseases which comprise novel cephalosporin derivatives as active components.

A further object of the present invention is to provide intermediate compounds in the synthesis of cephalosporin derivatives and processes for producing such intermediate compounds.

The present invention is based on the selection of a triazolopyrimidine ring as substituents at the 3-position of the cephem skeleton, and of groups containing a carboxy and hydroxy substituted phenylmethyloxyimino moiety, particularly a (carboxy substituted catechol)methyloxyimino moiety as substituents at the 7-position of the cephem skeleton. The compounds of the present invention containing these substituents have a wide antibacterial spectrum against Gram-negative bacteria and Gram-positive bacteria including methicillin-resistant *Staphylococcus aureus*. These compounds are extremely useful for the prevention and/or the treatment of infectious diseases.

DETAILED DESCRIPTION OF THE INVENTION

As a result of extensive investigations concerning development of cephalosporin derivatives having a satisfactory antibacterial activity against Gram-negative bacteria and also having strong antibacterial activity against Gram positive bacteria, the present inventors have found that cephalosporin derivatives represented by the general formula (I) satisfy these requirements and have accomplished the present invention.

The present invention is based on the selection of a triazolopyrimidine ring as substituents at the 3-position of the cephem skeleton, and of groups containing a carboxy and hydroxy substituted phenylmethyloxyimino moiety, particularly a (carboxy substituted catechol)methyloxyimino moiety, as substituents at the 7-position of the cephem skeleton.

The present invention is directed to cephalosporin derivatives represented by the general formula (I):

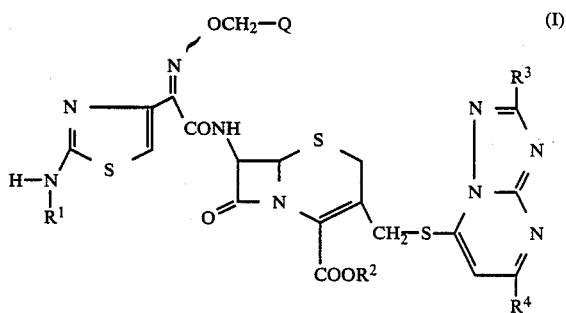

and non-toxic salts, solvates and non-toxic salts of solvates thereof; wherein $R^1$ represents a hydrogen atom or an amino-protecting group, $R^2$ represents a hydrogen atom or a carboxy-protecting group, $R^3$ represents a hydrogen atom, a hydroxy group, an amino group, a sulfo group, a carboxy group or a protected carboxy group, $R^4$ represents a hydrogen atom, a methyl group, a carboxy group, a protected carboxy group, a carboxymethyl group or a protected carboxymethyl group, Q represents a group:

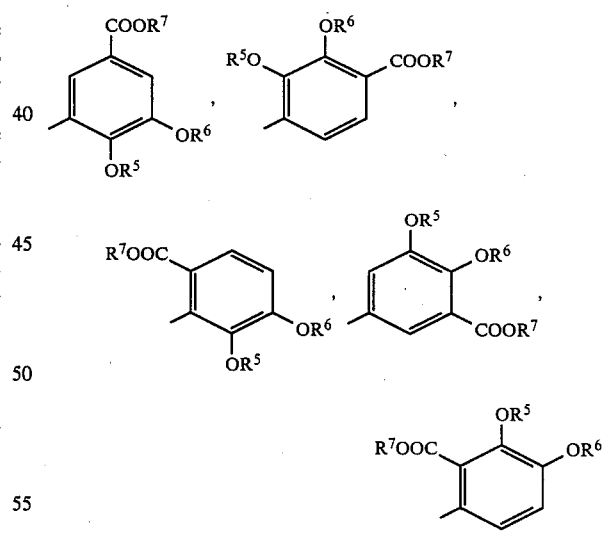

wherein $R^5$ and $R^6$ are same or different and represent a hydrogen atom, hydroxy-protecting group or together a vicinal diol protecting group, $R^7$ represents a hydrogen atom or carboxy-protecting group, and the bond shown with a wavy line represents a bond of anti-form or syn-form.

The present invention is also directed to the processes for preparing above-mentioned cephalosporin derivatives, and processes for producing such intermediate compounds. The present invention is further directed to pharmaceutical compositions for treating and/or preventing infectious diseases characterized by containing these cephalosporin derivatives as active components.

In the cephalosporin derivatives of the present invention represented by the general formula (I), it is known that the aminothiazole moiety as the substituent at the 7-position thereof exhibits tautomerism as shown below:

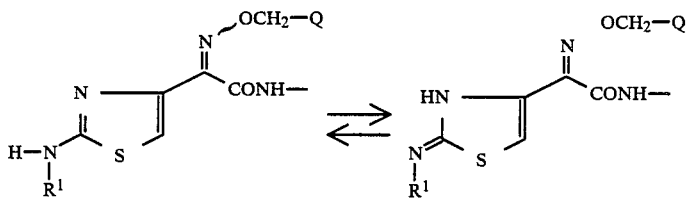

wherein R¹, Q and the bond shown with a wavy line have the same significance as defined above. In the present invention, the aminothiazole moiety is expressed as including both isomers since both are generally deemed to be the same substance. Accordingly, the compounds of the present invention represented by the general formula (I) also include both of these tautomeric isomers.

The compounds represented by the general formula (I) may form base or acid addition salts. Typical examples of base salts of the compounds represented by the general formula (I) include pharmaceutically acceptable salts such as alkali metal salts such as sodium salts, potassium salts, etc.; alkaline earth metal salts such as calcium salts, etc.; salts of organic bases such as ammonium salts, benzylamine salts, diethylamine salts, etc.; salts of amino acids such as arginine salts, lysine salts, etc. These salts of the compounds may be a mono-salts, di-salts or tri-salts. In the case of mono-salts or di-salts, the salts may be salts of the carboxy group at the 2-position and/or salts of the carboxy or sulfoxy group contained in the substituents at the 3-position, and/or salts of the carboxy group in the acyl group at the 7-position, of the cephem skeleton.

Typical examples of acid addition salts of the compounds represented by the general formula (I) include pharmaceutically acceptable salts, such as salts of inorganic acids such as hydrochlorides, hydrobromides, sulfates, phosphates, etc.; salts of organic acids such as acetates, citrates, maleates, tartarates, benzoates, ascorbates, ethanesulfonates, toluenesulfonates, etc.; salts of amino acids such as aspartates, glutamates, etc. These salts of the compounds may be a mono- or di-salts. In the case of mono-salts, the salt may be a salt of aminothiazole group in acyl group at 7-position or triazolopyrimidine group at 3-position of the cephem skeleton. The compounds of the present invention represented by the general formula (I) may be present as a syn-isomer shown below:

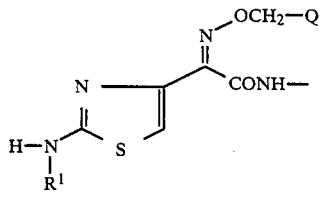

wherein R¹ and Q have the same significance as defined above; or as an anti-isomer shown below:

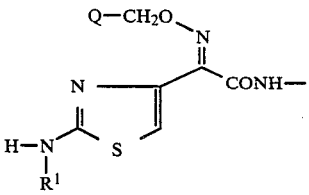

wherein R¹ and Q have the same significance as defined above; or as a mixture of these isomers. Among them, the syn-isomer is particularly preferred and, mixtures mainly composed of the syn-isomer are also preferred.

In the compounds of the present invention represented by the general formula (I), the amino-protecting groups may be selected from acyl groups such as formyl, acetyl, chloroacetyl, t-butoxycarbonyl, benzyloxycarbonyl, etc; or aralkyl groups such as benzyl, diphenylmethyl, triphenylmethyl, etc. Trimethylsilyl group may also be used as an amino-protecting group. The carboxy-protecting groups may be selected from alkyl esters such as methyl ester, ethyl ester, t-butyl ester, etc.; or aralkyl esters such as benzyl ester, diphenylmethyl ester, triphenylmethyl ester, etc.; or trimethylsilyl ester. Inorganic or organic bases may also be used as carboxy-protecting groups. The hydroxy-protecting groups may be selected from aralkyl group such as benzyl, etc.; or alkoxyalkyl groups such as methoxymethyl group, 1-methoxy-1-methylethyl group, etc.; or acyl groups such as acetyl group, chloroacetyl group, t-butoxycarbonyl group, benzyloxycarbonyl group, etc.; or alkyl groups such as methyl group, ethyl group, etc.; vicinal diol protecting group may be selected from substituted or unsubstituted alkylene group such as methylene group, oxomethylene group, isopropylidene group, etc. for protection of catechol group. Collectively taking account of various operations, synthesis of thus protected products, and conditions for the removal of protecting groups, it is preferred to use a triphenylmethyl group as the amino-protecting group and a diphenylmethyl group as the carboxy-protecting group, and an isopropylidene group as the hydroxy-protecting group.

The compounds of the present invention represented by the general formula (I) can be produced as follows. Namely;

Process A

The compounds of the present invention represented by the general formula (I) can be produced by reacting compounds represented by the general formula (II):

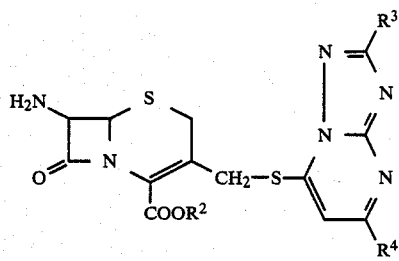

and salts thereof, wherein $R^2$, $R^3$ and $R^4$ have the same significance as defined above, with compounds represented by the general formula (III):

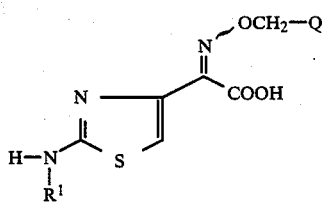

and salts thereof, wherein $R^1$, Q and the bond shown with a wavy line have the same significance as defined above.

If necessary and desired, the compounds represented by the general formula (II) may be converted into reactive derivatives at the amino group thereof, such as 7-trimethylsilylated derivatives.

The compounds represented by the general formula (II) may be reacted with the compounds represented by the general formula (III) using suitable condensing agents, for example, phosphorous oxychloride, N,N-dicyclohexylcarbodiimide, methyl-5-phenylisoxazolium-3'-sulfonate, etc. Alternatively, the compounds represented by the general formula (III) may be converted into appropriate reactive derivatives prior to the reaction with the compounds represented by the general formula (II). The appropriate reactive derivatives may be, for example, acid halides (e.g., acid chlorides), azides, acid anhydrides, particularly mixed acid anhydride with strong acids, active esters (e.g., N-hydroxysuccinimide ester) or active amides (e.g., imidazolide, triazolide).

The reaction between the compounds represented by the general formula (II) and the compounds represented by the general formula (III) may be carried out generally in an inert organic solvent such as dioxane, tetrahydrofuran, acetonitrile, chloroform, methylene chloride, ethyl acetate, dimethylformamide, etc., if necessary and desired, in the presence of deacidifying agents. The reaction may also be carried out in an aqueous solution, preferably in the presence of deacidifying agents. As the deacidifying agents, pyridine, triethylamine, diethylaniline, and the like may be used in the organic solvent system, and aqueous alkalis, preferably sodium hydroxide, sodium hydrogen carbonate, potassium carbonate, and the like may be used in the aqueous system.

The reaction may be carried out at temperatures ranging from about $-30°$ C. to room temperature, and preferably from $-10°$ C. to $10°$ C. Under the condition described above, the bond represented by a wavy line in the general formula (III) is retained.

The compounds represented by the general formula (II) used in the process of the present invention can be prepared by the method described in the Japanese Patent Kokai No. 142987 (1985). The compounds represented by the general formula (III):

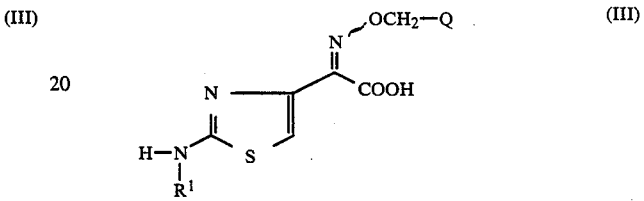

and salts thereof, wherein $R^1$, Q and the bond shown with a wavy line have the same significance as defined above, can generally be prepared by the methods D, E and F described below.

If necessary and desired, the protecting groups may be removed from thus obtained cephalosporin derivatives represented by the general formula (I).

Process B

The compounds represented by the general formula (I) can be produced by reacting compounds represented by the general formula (IV):

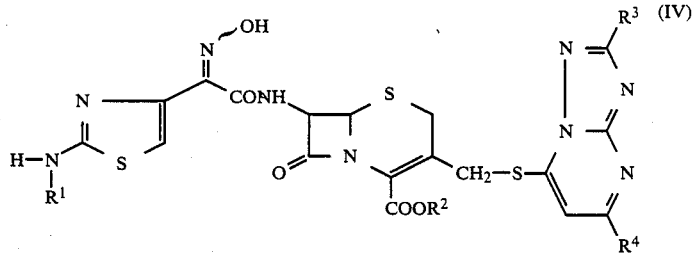

and salts thereof, wherein $R^1$, $R^2$, $R^3$, $R^4$ and the bond shown with a wavy line have the same significance as defined above, with compounds represented by the general formula (V):

and salts thereof, wherein Q have the same significance as defined above, and X represents a halogen atom or a hydroxy group. When the compounds represented by the general formula (V) are alcohols, they may be either reacted directly with the compounds represented by the general formula (IV) in the presence of appropriate condensing agents such as triphenylphosphine and ethyl azodicarboxylate, or converted into appropriate reactive derivatives such as tosylate and then reacted with the compounds represented by the general formula (IV). However, with regard to reactivity and operability, halides are preferred for the compounds represented by the general formula (V) to be reacted with the compounds represented by the general formula (IV).

The reaction between the compounds represented by the general formula (IV) and the compounds represented by the general formula (V) may be carried out in an inert organic solvent such as dioxane, tetrahydrofuran, acetonitrile, chloroform, methylene chloride, ethyl acetate, dimethylformamide, etc. or mixture thereof, or, if necessary and desired, in water or mixture of water and organic solvents, preferably in the presence of deacidifying agents. As the deacidifying agents, triethylamine, diethylaniline and the like may be used in organic solvents, and aqueous alkalis, preferably sodium hydroxide, sodium hydrogen carbonate, potassium carbonate and the like may be used in aqueous solvents.

The reaction between the compounds represented by the general formula (IV) and the compounds represented by the general formula (V) may be carried out at temperatures in the range of from about $-30°$ C. to room temperature and preferably from $-10°$ C. to $10°$ C. Under the conditions described above, the bond shown with a wavy line in the general formula (IV) is retained.

The compounds represented by the general formula (IV) can be prepared by the method described in the Japanese patent application No. 249193 (1984).

The compounds represented by the general formula (V), in halide form, can be prepared, for example, from 2,3-dihydroxy-4-methylbenzoic acid, 2,3-dihydroxy-5-methylbenzoic acid, 2,3-dihydroxy-6-methylbenzoic acid by the following general procedure; firstly, protection of the hydroxyl groups, then protection of the carboxy group by esterification, and finally halogenation of the benzyl terminus by a conventional method. The resultant halides can be hydrolized to give the compounds represented by the general formula (V) in hydroxyl form. Also, the compounds represented by the general formula (V), in halide form, can be prepared, for example, from 2,2,4-trimethylbenzodioxol by the following procedure; firstly, acetylation, then oxidation of acetyl group, then protection of the carboxy group by esterification, and finally halogenation of the benzyl terminus by a conventional method. The resultant halides can be hydrolyzed to give the compounds represented by the general formula (V) in hydroxyl form.

If necessary and desired, the protecting groups may be removed from thus obtained cephalosporin derivatives represented by the general formula (I).

Process C

The compounds represented by the general formula (I) can be produced by reacting compounds represented by the general formula (VI):

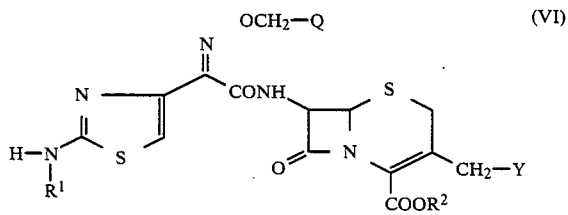
(VI)

and salts thereof, wherein $R^1$, $R^2$, Q and the bond shown with a wavy line have the same significance as defined above, and Y represents an acetoxy group or a halogen atom, with compounds represented by the general formula (VII):

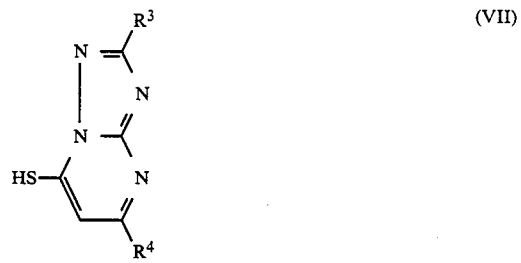
(VII)

and salts thereof, wherein $R^3$ and $R^4$ have the same significance as defined above. The reaction can be carried out by reacting the compounds represented by the general formula (VI) with the compounds represented by the general formula (VII) in an organic solvent such as alcohols, dimethylformamide, acetonitrile, etc. or mixture thereof, or in an aqueous system. The reaction of the compounds represented by the general formula (VI) and the compounds represented by the general formula (VII) may be carried out in an organic solvent, preferably in the presence of Lewis acid, such as boron trifluoride-ether complex and the like, or in an aqueous system in the presence of an appropriate amount of aqueous alkali, such as sodium hydrogen carbonate or potassium carbonate, preferably in a buffer solution at a pH in the range of 6.0 to 7.8, at temperatures in the range of about $40°$ C. to about $80°$ C., preferably at from $55°$ to $65°$ C. Under the condition described above, the bond represented by a wavy line in the general formula (VI) is retained. The compounds represented by the general formula (VI) can be prepared from the compounds represented by the general formula (III) and known 7-aminocephalosporanic acids or derivatives thereof by conventional condensation reaction. The compounds represented by the general formula (VII) can be prepared by the method described in the Japanese Patent Kokai No. 142987 (1985).

If necessary and desired, the protecting groups may be removed from thus obtained cephalosporin derivatives represented by the general formula (I).

Process D

The compounds represented by the general formula (III) can be produced by reacting the known compounds represented by the general formula (VIII):

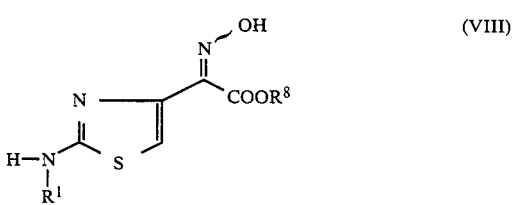
(VIII)

and salts thereof, wherein $R^1$ and the bond shown with a wavy line have the same significance as defined above, and $R^8$ represents a hydrogen atom or a carboxy-protecting group, with the compounds represented by the general formula (V):

$X-CH_2-Q$ (V)

and salts thereof, wherein Q and X have the same significance as defined above, followed by removal of $R^8$ by conventional methods such as alkali hydrolysis. When the compounds represented by the general formula (V) are alcohols, they may be either reacted directly with the compounds represented by the general formula (VIII) in the presence of appropriate condensing agents such as triphenylphosphine and ethyl azodicarboxylate, or converted into appropriate reactive derivatives such as tosylate and then reacted with the compounds represented by the general formula (VIII). However, with regard to reactivity and operability, halides are preferred for the compounds represented by the general formula (V) to be reacted with the compounds represented by the general formula (VIII).

The reaction between the compounds represented by the general formula (VIII) and the compounds represented by the general formula (V) may be carried out in an inert organic solvent such as dioxane, tetrahydrofuran, acetonitrile, chloroform, methylene chloride, ethyl acetate, dimethylformamide, etc. or mixture thereof, or, if necessary and desired, in water or mixture of water and organic solvents, preferably in the presence of deacidifying agents. As the deacidifying agents, triethylamine, diethylaniline and the like may be used in organic solvents, and aqueous alkalis, preferably sodium hydroxide, sodium hydrogen carbonate, potassium carbonate and the like may be used in aqueous solvents.

The reaction between the compounds represented by the general formula (VIII) and the compounds represented by the general formula (V) may be carried out at temperatures in the range of from about $-30°$ C. to room temperature, and preferably from $-10°$ C. to $10°$ C. Under the condition described above, the bond represented by a wavy line in the general formula (VIII) is retained.

The compounds represented by the general formula (V) can be prepared from, for example, 2,2,4-trimethylbenzodioxol, 2,3-dihydroxy-4-methylbenzoic acid, 2,3-dihydroxy-5-methylbenzoic acid or 2,3-dihydroxy-6-methylbenzoic acid by the method described above for the compounds represented by the general formula (VI).

Process E

The compounds represented by the general formula (III) can be prepared by reacting the known compounds represented by the general formula (IX):

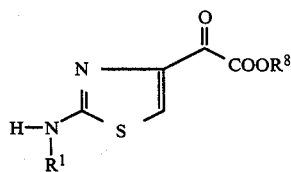

(IX)

and salts thereof, wherein $R^1$ and $R^8$ have the same significance as defined above, with the compounds represented by the formula (X):

$$H_2NOCH_2-Q \qquad (X)$$

and salts thereof, wherein Q has the same significance as defined above, in an organic solvents, such as methanol, ethanol, dioxane, tetrahydrofuran, methylene chloride and ethyl acetate, and if necessary and desired, in the presence of dehydrating agents such as molecular sieve, at temperatures in the range of from about $-30°$ C. to about $100°$ C., preferably from $-10°$ C. to $30°$ C., followed by removal of $R^8$ by conventional methods such as alkali hydrolysis.

The compounds represented by the general formula (X) can be prepared from a halide form of the above-mentioned compounds represented by the general formula (V) by phthaloyloxidization followed by dephthaloylization, both of which can be carried out conventional methods.

Process F

The compounds represented by the general formula (III) can be prepared by reacting the known compounds represented by the general formula (XI):

(XI)

and salts thereof, wherein $R^8$ has the same significance as defined above, and Z represents a halogen atom, with the compounds represented by the general formula (V):

(V)

and salts thereof, wherein Q and X have the same significance as defined above, by the method same as above-mentioned process D, then by condensing the product with the thiourea derivatives represented by the general formula (XII):

(XII)

and salts thereof, wherein $R^1$ have the same significance as defined above, followed by removal of $R^8$ by conventional methods such as alkali hydrolysis. Under the condition described above, the bond represented by a wavy line in the general formula (XI) is retained. With regard to reactivity and operability, it is desirable to react an alcohol form of the compounds represented by the general formula (V) with the compounds represented by the general formula (XI).

In the present process, the condensation with thiourea derivatives can be carried out in an organic solvent such as methanol, ethanol, dioxane, tetrahydrofuran, methylene chloride and ethyl acetate, or mixture thereof, and preferably in the presence of deacidifying agent such as triethylamine, diethylaniline, sodium hydrogen carbonate and potassium carbonate, at temperatures in the range of from about $-30°$ C. to about $100°$ C., preferably from $-10°$ C. to $30°$ C. Under the condition described above, the bond represented by a wavy line in the general formula (XI) is retained.

The compounds of the present invention show a potent antibacterial activity against a wide range of bacteria including Gram-positive and Gram-negative bacteria, and also against methicillin-resistant *Staphylococcus aureus*, and are quite useful as therapeutic agents from infectious diseases.

To demonstrate the utility of the compounds of the present invention, data on antibacterial activity of a representative compound are shown below.

Compound 1: (6R,7R)-7-[2-(2-amino-4-thiazolyl)-2-[Z-[(6-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 2: (6R,7R)-7-[2-(2-amino-4-thiazolyl)-2-]Z-[(5-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 3: (6R,7R)-7-[2-(2-amino-4-thiazolyl)-2-[Z-[(3-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 4: (6R,7R)-7-[2-(2-amino-4-thiazolyl)-2-[Z-[(2-carboxy-3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 5: (6R,7R)-7-[2-(2-amino-4-thiazolyl)-2-[Z-[(4-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid

EXPERIMENTAL EXAMPLE 1

Antibacterial activity in vitro was determined in accordance with the agar plate dilution method.

A platinum loop each of test bacteria ($10^6$ cells/ml), cultured in Mueller Hinton broth, was inoculated on Mueller Hinton agar plates which contained test compounds at various concentrations. After cultivating at 37° C. for 20 hours, the minimum inhibitory concentration (MIC μg/ml) was determined.

TABLE 1

| Compound No. | MIC (μg/ml) | | | | |
|---|---|---|---|---|---|
| | Staphylococcus aureus 209P | Escherichia coli NIHJ JC 2 | Serratia marcescens IFO 3759 | Klebsiella pneumoniae IFO 3317 | Pseudomonas aeruginosa 34 |
| 1 | 6.25 | 0.78 | 0.39 | <0.05 | 0.20 |
| 2 | 6.25 | 0.39 | 0.10 | 0.05 | 0.20 |
| 3 | 6.25 | 0.78 | 0.78 | 0.10 | N.D. |
| 4 | 3.13 | 0.39 | 0.39 | 0.05 | N.D |
| 5 | 3.13 | 0.78 | 0.78 | 0.05 | N.D. |
| CAZ* | N.D. | 0.20 | <0.05 | <0.05 | 3.13 |

N.D.; Not determined.
*; Ceftazidime

As shown in Table 1, these compounds were active against Gram-positive and negative bacteria.

EXPERIMENTAL EXAMPLE 2

Protection ability against systemic bacterial infection was determined as follows. An aqueous suspension of test bacteria was intraperitoneally injected into 10 four week old ICR mice. One hour after the infection, test compounds were intravenously administered. The number of surviving mice was counted 1 week after injection to determine the dose at which 50% of the test animals were alive ($ED_{50}$: mg/kg).

TABLE 2

| Compound No. | $ED_{50}$ (mg/Kg) | | | | | | | |
|---|---|---|---|---|---|---|---|---|
| | Staphylococcus aureus | | Escherichia coli | Serratia marcescens | Enterobacter | Klebsiella pneumoniae IFO | Pseudomonas aeruginosa IFO | |
| | 58[1] | 4[1] | 67 | 274 | 8 | 3317 | 3445 | 34 |
| 1 | 15.9 | N.D. | 1.59 | 0.50 | 1.28 | 0.55 | 52 | N.D. |
| 2 | 9.65 | N.D. | 1.10 | 0.55 | 1.31 | 0.34 | 33.7 | N.D. |
| 3 | N.D. | 2.08 | N.D. | 0.72 | N.D. | N.D. | N.D. | 46.8 |
| 4 | N.D. | 3.35 | N.D. | 0.97 | N.D. | N.D. | N.D. | 50.6 |
| 5 | N.D. | 4.21 | N.D. | 0.75 | N.D. | N.D. | N.D. | 81.2 |
| CMD[2] | 18.9 | 5.94 | N.D. | N.D. | N.D. | N.D. | N.D. | N.D. |
| CAZ[3] | N.D. | N.D. | 2.80 | 3.62 | 4.36 | 1.73 | 230 | 123 |

N.D.; Not determined.
[1]; Methicillin-resistant strain
[2]; Cefamandole
[3]; Ceftazidime As shown in Table 2, these compounds were evidently more potent than the reference compound in protecting the animals from experimental infection.

Next, $LD_{50}$ of representative examples of the compounds of the present invention is shown in Table 3 wherein $LD_{50}$ was determined in accordance with the Probit method.

TABLE 3

| compound | $LD_{50}$ (mg/Kg, i.v.) |
|---|---|
| Compound 1 | >4000 |
| 2 | >4000 |
| 3 | >4000 |
| 4 | >4000 |
| 5 | >4000 |

The compounds of the present invention are active against microorganisms, such as Gram-positive aerobic bacteria such as Staphylococcus aureus, streptococci, etc., Gram-negative aerobic bacteria such as Escherichia coli, Klebsiella pneumoniae, Proteus mirabilis, Proteus morganii, Serratia marcescens, Pseudomonas aeruginosa, Citrobacter, Enterobacter, Flavobacter, etc., and these compounds are also thought to be highly safe and useful for the treatment of infectious diseases caused by these microorganisms.

The cephalosporin derivatives provided by the present invention can be employed as pharmaceutical compositions, for example, in the form of pharmaceutical compositions containing cephalosporin derivatives together with appropriate, pharmaceutically acceptable carriers, etc. The pharmaceutical composition may take a solid form, such as tablets, capsules, etc. or a liquid form, such as injections, etc. The compositions may be sterilized and may contain auxiliary agents generally employed in the pharmaceutical art, such as sodium hydrogen carbonate, citric acid, propylene glycol, Tween 80, etc.

Further, it is also preferred to use the compounds of the present invention after they are formed into freeze-dried products or powders followed by dissolving them in a conventional solvent, e.g., water or physiological saline, before use. The compounds can be used orally or parenterally. While dose varies depending upon age and conditions of the patient, conditions and kind of diseases, etc., from about 0.01 to about 10 g, preferably from about 0.1 to about 5 g, can be used as a daily dose for an adult. Parenteral administration of the compounds provided by the present invention is particularly preferred.

Hereafter the present invention will be described with reference to the examples below but is not deemed to be limited thereof.

EXAMPLE 1

Preparation of (6R,7R)-7-[2-(2-amino-4-thiazolyl)-2-[Z-[(5-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 2).

Step 1

Preparation of 6-acethyl-2,2,4-trimethylbenzodioxol

To a solution of 2,2,4-trimethylbenzodioxol (50 g) in acetic anhydride (250 ml) was added zinc chloride under ice cooling, and the solution was stirred at 0° C. for 2 hours and for 2.5 hours at room temperature. The reaction mixture was concentrated under reduced pressure, and poured into ice-water (300 ml) then extracted with ether (400 ml). The aqueous layer was extracted with ether (200 ml). The organic layer was combined and washed four times with water (150 ml each), twice with aqueous solution of saturated sodium hydrogen carbonate (150 ml) and once with brine (150 ml). The washed solution was dried over anhydrous sodium sulfate. The dried solution was concentrated under reduced pressure, and the residue was purified by silica gel column chromatography to give 14.8 g of the objective compound.

IR (neat; cm$^{-1}$): 1676, 1426, 1302, 1210.
NMR (CDCl$_3$; ppm): 7.4 (1H, s), 7.2 (1H, s), 2.5 (3H, s), 2.2 (3H, s), 1.7 (6H, s).

Step 2

Preparation of 2,2,4-trimethylbenzodioxol-6-carboxylic acid.

To a suspension of calcium hypochlorite (40.3 g) warmed to 60° C., was added a solution of sodium carbonate (28.2 g) and sodium hydroxide (8.2 g) in water (80 ml). After stirring a solution for 5 minutes, the solution was filtered. The filtrate was warmed to 55° C., to this was added the compound (14 g) obtained in step 1. After the addition, the reaction mixture was stirred at 70° C. for 2 hours, and then cooled with ice. To this solution was added a solution of sodium bisulfite (8.2 g) in water (40 ml) followed by stirring for 1 hour. The solution was extracted with ether (100 ml), and the aqueous layer was acidified to pH 2 with aqueous hydrochloric acid. The precipitated solid was filtered and washed with water (100 ml), and dried to give 11.7 g of the objective compound.

IR (KBr; cm$^{-1}$): 1683, 1418, 1309.
NMR (CDCl$_3$; ppm): 7.5 (1H, s), 7.3 (1H, s), 2.2 (3H, s), 1.7 (6H, s).

Step 3

Preparation of tertiary (t)-butyl 2,2,4-trimethylbenzodioxol-6-carboxylate.

To a suspension of the product obtained in Step 2 (11.7 g) in benzene (100 ml) were added thionyl chloride (16 ml) and N,N-dimethylformamide (5 drops), and the mixture was stirred at 60° C. for 30 minutes. The solvent was removed under reduced pressure, and the residue was dissolved in methylene chloride (50 ml). The solution was then added dropwise to an ice-cooled mixture of t-butanol (52 ml) and pyridine (27 ml), and the mixture was stirred at room temperature for 15 hours. After removing the solvent under reduced pressure, ether (300 ml) was added to the residue. The ether solution was washed twice with water (150 ml each), twice with aqueous hydrochloric acid (1N, 150 ml each), twice with saturated aqueous solution of sodium hydrogen carbonate (100 ml) and once with brine (100 ml), and the washed solution was dried over anhydrous sodium sulfate. The dried solution was concentrated under reduced pressure to give 13.7 g of the objective compound.

IR (neat; cm$^{-1}$): 1702, 1315, 1234, 1219, 1122.
NMR (CDCl$_3$; ppm): 7.4 (1H, s), 7.2 (1H, s), 1.71 (3H, s), 1.68 (6H, s), 1.6 (9H, s).

Step 4

Preparation of t-butyl 4-bromomethyl-2,2-dimethylbenzodioxol-6-carboxylate.

To a solution of the product obtained in Step 3 (13.6 g) in carbon tetrachloride (75 ml) were added N-bromosuccinimide (9.2 g) and benzoyl peroxide (32 mg), and the mixture was refluxed for 80 minutes. The reaction mixture was then cooled to room temperature and insoluble matter was removed by filtration. The filtrate was washed once with saturated aqueous solution of sodium hydrogen carbonate (50 ml), once with brine (50 ml) and dried over anhydrous sodium sulfate. The dried solution was concentrated under reduced pressure, and the residue was crystallized with n-hexane to give 11.5 g of the objective compound.

IR (neat; cm$^{-1}$): 1708, 1446, 1312, 1242, 1138, 1115.
NMR (CDCl$_3$; ppm): 7.6 (1H, d, J=2 Hz), 7.3 (1H, d, J=2 Hz), 4.4 (2H, s), 1.7 (6H, s), 1.6 (9H, s).

Step 5

Preparation of t-butyl 2,2-dimethyl-4-(N-phthaloyloxymethyl)benzodioxol-6-carboxylate.

To a solution of the product obtained in Step 4 (9.0 g) in acetonitrile (50 ml) was added dropwise a solution of N-hydroxyphthalimide (4.7 g) and triethylamine (4.0 ml) in acetonitrile (50 ml) at room temperature, and the mixture was stirred for 4 hours. The reaction mixture was poured into ice water (250 ml) and extracted with ether (once with 300 ml, then twice with 100 ml). The organic layer was washed thrice with aqueous solution of sodium hydrogen carbonate, and once with brine (150 ml). The washed solution was dried over anhydrous sodium sulfate. The dried solution was concentrated under reduced pressure, and the residue was crystallized with ether to give 7.7 g of the objective compound.

IR (KBr; cm$^{-1}$): 1800, 1730, 1700, 1242.
NMR (CDCl$_3$; ppm): 7.7 (4H, m), 7.6 (1H, d, J=2 Hz), 7.3 (1H, d, J=2 Hz), 5.2 (2H, s), 1.5 (15H, s).

Step 6

Preparation of t-butyl 4-aminooxymethyl-2,2-dimethylbenzodioxol-6-carboxylate.

To a solution of the product obtained in Step 5 (6.2 g) in methylene chloride (80 ml) and the solution was cooled to −30° C. To the cold solution was added a solution of methylhydrazine (0.74 g) in methylene chloride (20 ml), and the mixture was stirred for 1.5 hour under ice cooling. Insoluble matter was filtered off, and the filtrate was concentrated under reduced pressure. The residue was purified by silica gel column chromatography to give 7.6 g of the objective compound.

NMR (CDCl₃; ppm): 7.6 (1H, d, J=2 Hz), 7.3 (1H, d, J=2 Hz), 5.5 (2H, bs), 4.7 (2H, s), 1.7 (6H, s), 1.6 (9H, s).

Step 7

Preparation 2-(2-amino-4-thiazolyl)-2-[Z-[(6-t-butoxycarbonyl-2,2-dimethylbenzodioxol-4-yl)methyl]oxyimino]acetic acid.

To a solution of the product obtained in Step 6 (4.1 g) in N,N-dimethylformamide (25 ml) was added (2-aminothiazol-4-yl)glyoxylic acid (2.4 g), and the mixture was stirred at room temperature for 90 minutes. The reaction mixture was concentrated under reduced pressure, and the residue was dissolved in ethyl acetate (300 ml). The solution was washed twice with water (150 ml each) and dried over anhydrous sodium sulfate. The dried solution was concentrated under reduced pressure, and the residue was crystallized with ether to give 4.7 g of the objective compound.

IR (KBr; cm⁻¹): 1715, 1648, 1636, 1311.

NMR (DMSO-d₆; ppm): 7.6 (1H, d, J=1 Hz), 7.3 (3H, s), 6.9 (1H, s), 5.1 (2H, s), 1.7 (6H, s), 1.5 (9H, s).

Step 8

Preparation of (6R,7R)-7-[2-(2-amino-4-thiazolyl)-2-[Z-[(6-t-butoxycarbonyl-2,2-dimethylbenzodioxol-4-yl)methyl]oxyimino]acetamido]-3-[(2-diphenylmethyloxycarbonyl-5-methyl-s-triazolo [1,5-a]pyrimidin-7-yl)thiomethyl]-8-oxo-5-thia-1-azabicyclo[4.2.0]-oct-2-ene-2-carboxylic acid diphenylmethyl ester.

To a solution of the product obtained in Step 7 (3.5 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (5.0 g) in methylene chloride (90 ml) was added N,N-dicyclohexylcarbodiimide (1.7 g), and the mixture was stirred for 12 hours at room temperature. Insoluble matter was filtered off, and the filtrate was then concentrated under reduced pressure. The residue was dissolved in ethyl acetate (300 ml), washed twice with water (100 ml each), twice with brine (100 ml each) and dried over anhydrous sodium sulfate. The dried solution was concentrated under reduced pressure, and the residue was purified by silica gel column chromatography to give 3.0 g of the objective compound.

IR (KBr; cm⁻¹): 1791, 1735, 1508, 1307, 1239.

NMR (DMSO-d₆; ppm): 9.8 (1H, d, J=8 Hz), 7.6–6.7 (28H, m), 5.9 (1H, dd, J=8, 5 Hz), 5.3 (2H, d, J=5 Hz), 5.1 (2H, s), 4.3 (2H, s), 3.7 (2H, ABq), 2.6 (3H, s), 1.7 (6H, s), 1.5 (9H, s).

Step 9

Preparation of (6R,7R)-7-[2-(2-amino-4-thiazolyl)-2-[Z-[(5-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a mixture of trifluoroacetic acid (20 ml) and anisole (2 ml) was added the product obtained in step 8 (2.9 g) under ice cooling. The mixture was stirred for 6 hours at room temperature. The reaction mixture was then poured into ether (100 ml). The precipitated crystals were suspended in water (25 ml) and the pH of the suspension was adjusted to 8.0 with sodium hydrogen carbonate. The resultant solution was applied to a Diaion HP-20 column and eluted with water. Fractions containing the objective compound were collected and concentrated under reduced pressure to 5 ml. The concentrate was crystallized by pouring into ethanol (50 ml) to give 0.74 g of the objective compound.

IR (KBr; cm⁻¹): 1762, 1598, 1516, 1399, 1314.

NMR (D₂O; ppm): 7.5 (1H, d, J=2 Hz), 7.4 (1H, d, J=2 Hz), 7.1 (1H, s), 7.0 (1H, s), 5.7 (1H, d, J=5 Hz), 5.3 (2H, s), 5.0 (1H, d, J=5 Hz), 4.3 (2H, ABq), 3.4 (2H, ABq), 2.6 (3H, s).

EXAMPLE 2

Preparation of (6R,7R)-7-[2-(2-amino-4-thiazolyl)-2-[Z-[(5-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

Step 1

Preparation of ethyl 2-(2-amino-4-thiazolyl)-2-[Z-[(6-t-butoxycarbonyl-2,2-dimethylbenzodioxol-4-yl)methyl]oxyimino]acetate.

To a solution of ethyl 2-(2-amino-4-thiazolyl)-2-(Z-hydroxyimino)acetate (1 g) in dry N,N-dimethylformamide (10 ml) was added sodium hydride (60% dispersion in mineral oil; 200 mg) under ice cooling, and the mixture was stirred for 15 minutes. To the mixture was added dropwise a solution of the product obtained in Step 4 of Example 1 (1.9 g) in N,N-dimethylformamide (10 ml). The mixture was stirred under ice cooling for 1.5 hours. The reaction mixture was then poured into an ice-cooled mixture of aqueous hydrochloric acid (1 N, 200 ml) and ethyl acetate (200 ml), and stirred vigorously. The organic layer was separated and washed once with saturated aqueous solution of sodium hydrogen carbonate (100 ml) and thrice with brine (100 ml each). The washed solution was dried over anhydrous sodium sulfate. The dried solution was concentrated under reduced pressure, and the residue was crystallized with hexane (50 ml) to give 1.78 g of the objective compound.

NMR (CDCl₃; ppm): 7.6 (1H, d, J=2 Hz), 7.3 (1H, d, J=2 Hz), 6.7 (1H, s), 5.7 (2H, bs), 5.3 (2H, s), 4.4 (2H, q, J=7 Hz), 1.7 (6H, s), 1.6 (9H, s), 1.4 (3H, t, J=7 Hz).

Step 2

Preparation 2-(2-amino-4-thiazolyl)-2-[Z-[(6-t-butoxycarbonyl-2,2-dimethylbenzodioxol-4-yl)methyl]oxyimino]acetic acid.

To a suspension of the product of Step 1 (1 g) in ethanol (6 ml) was added an aqueous solution of sodium hydroxide (conc. 2N, 2.1 ml), and the mixture was stirred for 2 hours at room temperature, then for 1 hour at 63° C. The reaction mixture was concentrated under reduced pressure, and water (20 ml) was added to the residue. The mixture was acidified with aqueous hydrochloric acid (1 N) to pH 3, then extracted with ethyl acetate (50 ml). The extract was washed twice with brine (30 ml each) and dried over anhydrous sodium sulfate. The dried solution was concentrated under reduced pressure, and the residue was crystallized with ether-hexane (1:1, 30 ml) to give 840 mg of the objective compound.

IR (KBr; cm⁻¹): 1715, 1648, 1636, 1311.

NMR (DMSO-d₆; ppm): 7.6 (1H, d, J=1 Hz), 7.3 (3H, s), 6.9 (1H, s), 5.1 (2H, s), 1.7 (6H, s), 1.5 (9H, s). These data are in complete agreement with those of Step 7 of Example 1.

Step 3

Preparation of (6R,7R)-7-[2-(2-amino-4-thiazolyl)-2-[Z-[(5-carboxy-2,3-dihydroxyphenyl)methyl]ox-yimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The compound of the title given above was prepared from the product of Step 2, according to the methods of Steps 8 and 9 of Example 1.

IR (KBr; cm$^{-1}$): 1762, 1598, 1516, 1399, 1314.

NMR (D$_2$O; ppm): 7.5 (1H, d, J=2 Hz), 7.4 (1H, d, J=2 Hz), 7.1 (1H, s), 7.0 (1H, s), 5.7(1H, d, J=5 Hz), 5.3 (2H, s), 5.0 (1H, d, J=5 Hz), 4.3 (2H, ABq), 3.4 (2H, ABq), 2.6 (3H, s). These data are in complete agreement with those of Step 9 of Example 1.

According to the method described in Example 1, compounds of Examples 3 and 4, described below, were prepared. According to the method described in Example 2, compounds of Examples 5 and 6, described below, were prepared.

EXAMPLE 3

(6R,7R)-7-[2-(2-amino-4-thiazolyl)-2-[Z-[(5-carboxy-2,3-dihydroxyphenyl)methyl]ox-yimino]acetamido]-3-[(5-methyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1598, 1516, 1399, 1314.

NMR (D$_2$O; ppm): 8.5 (1H, s), 7.42 (1H, d, J=2 Hz), 7.36 (1H, d, J=2 Hz), 7.1 (1H, s), 7.0 (1H, s), 5.6 (1H, d, J=5 Hz), 5.2 (2H, s), 5.0 (1H, d, J=5 Hz), 4.3 (2H, ABq), 3.4 (2H, ABq), 2.6 (3H, s).

EXAMPLE 4

(6R,7R)-7-[2-(2-amino-4-thiazolyl)-2-[Z-[-(5-carboxy-2,3-dihydroxyphenyl)methyl]ox-yimino]acetamido]-3-[(5-carboxy-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1763, 1598, 1534, 1398.

NMR (D$_2$O; ppm): 8.5 (1H, s), 7.5 (1H, d, J=2 Hz), 7.2 (1H, d, J=2 Hz), 7.1 (1H, s), 7.0 (1H, s), 5.7 (1H, d, J=5 Hz), 5.3 (2H, s), 5.0 (1H, d, J=5 Hz), 4.3 (2H, ABq), 3.4 (2H, ABq).

EXAMPLE 5

(6R,7R)-7-[2-(2-amino-4-thiazolyl)-2-[Z-[(5-carboxy-2,3-dihydroxyphenyl)methyl]ox-yimino]acetamido]-3-[(5-carboxymethyl-s-triazolo-[1,5-a]pyrimidin-7-yl)thiomethyl]-8-oxo-5-thia-1-azabicyclo[4.2.0]oct-2-ene-2-carboxylic acid IR (KBr; cm$^{-1}$): 1763, 1595, 1515, 1394, 1354.

NMR (D$_2$O; ppm): 8.5 (1H, s), 7.43 (1H, d, J=2Hz), 7.38 (1H, d, J=2Hz), 7.1 (1H, s), 7.0 (1H, s), 5.6 (1H, d, J=5 Hz), 5.3 (2H, s), 5.0 (1H, d, J=5 Hz), 4.3 (2H, ABq), 3.4 (2H, ABq), 2.6 (2H,s).

EXAMPLE 6

(6R,7R)-7-[2-(2-amino-4-thiazolyl)-2-[Z-[(5-carboxy-2,3-dihydroxyphenyl)methyl]ox-yimino]acetamido]-3-[(2-sulfo-5-methyl-s-tri-azolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1596, 1512, 1399.

NMR (D$_2$O; ppm): 7.5 (1H, d, J=2 Hz), 7.4 (1H, d, J=2 Hz) 7.1 (1H, s), 7.0 (1H, s), 5.7 (1H, d, J=5 Hz) 5.3 (2H, s), 5.0 (1H, d, J=5 Hz), 4.3 (2H, ABq), 3.4 (2H, ABq), 2.6 (3H, s).

EXAMPLE 7

Preparation of (6R,7R)-7-[2-(2-amino-4-thiazolyl)-2-[Z-[(4-carboxy-2,3-dihydroxyphenyl)methyl]ox-yimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 5).

Step 1

Preparation of methyl 2,2,7-trimethylbenzodioxol-4-carboxylate.

To a solution of methyl 2,3-dihydroxy-4-methy benzoate (33 g) in acetone (900 ml) was added phosphorous pentoxide (two times, 30 g each, interval 30 minutes) while stirring vigorously. After addition, stirring was continued for further 30 minutes, and the resultant solution was decanted. The decanted solution was concentrated under reduced pressure. The residue was dissolved in ether (400 ml), washed once with saturated aqueous solution of sodium hydrogen carbonate (150 ml) and once with brine (150 ml) and dried over anhydrous sodium sulfate. The dried solution was concentrated under reduced pressure. The residue was added to n-hexane (300 ml), and precipitated matter was filtered off. The filtrate was washed twice with aqueous solution of sodium hydroxide (1N, 100 ml each, once with brine (100 ml) and dried over anhydrous sodium sulfate. The dried solution was concentrated under reduced pressure and the residue was purified by silica gel column chromatography to give 7.5 g of the objective compound.

IR(KBr; cm$^{-1}$): 1709, 1460, 1426, 1301, 1250, 1207, 1112.

NMR (CDCl$_3$; ppm): 7.3 (1H, d, J=8 Hz), 6.6 (1H, d, J=8 Hz), 3.9 (3H, s), 2.2 (3H, s), 1.7 (6H, s).

Step 2

Preparation of 2,2,7-trimethylbenzodioxol-4-carboxylic acid.

To a suspension of the compound (7.5 g) obtained in Step 1 in ethanol (100 ml), was added aqueous solution of potassium hydroxide (3N, 22 ml). After refluxing for 30 minutes, the reaction mixture was concentrated under reduced pressure to ca. 30 ml, and dissolved with water (200 ml) followed by washing once with ether (150 ml). The aqueous layer was acidified to pH 3 with aqueous hydrochloric acid (4N), and extracted twice with ethyl acetate (250 ml, 100 ml each). The extracts was washed twice with brine (100 ml each), and dried over anhydrous sodium sulfate. The dried solution was concentrated under reduced pressure. The residue was washed with n-hexane (100 ml) to give 6.5 g of the objective compound.

IR (KBr; cm$^{-1}$): 1685, 1648, 1484, 1313, 1254, 1220, 1207, 767.

NMR (CDCl$_3$; ppm): 7.3 (1H, d, J=8 Hz), 6.7 (1H, d, J=8 Hz) 2.2 (3H, s), 1.7 (6H, s).

Step 3

Preparation t-butyl 2,2,7-trimethylbenzodioxol-4-carboxylate.

To a suspension of the product obtained in Step 2 (6.4 g) in benzene (50 ml) were added thionyl chloride (8 ml) and N,N-dimethylformamide (3 drops). After stirring at 40° C. for 90 minutes the solvent was removed under reduced pressure. The residue was dissolved in methylene chloride (25 ml), and added dropwise to an ice-cooled mixture of t-butanol (25 ml) and pyridine (13 ml). After stirring at room temperature for 17 hours, the solvent was removed under reduced pressure. The residue was dissolved in ether (300 ml), and the ether solution was washed once with water (150 ml), twice with aqueous hydrochloric acid (1N, 100 ml each), twice with saturated aqueous solution of sodium hydrogen carbonate (100 ml each), and once with brine (100 ml), then dried over anhydrous sodium sulfate. The dried solution was concentrated under reduced pressure to give 7.2 g of the objective compound.

IR (KBr; cm$^{-1}$): 1712, 1466, 1427, 1300, 1255, 1234, 1152, 1074.

NMR (CDCl$_3$; ppm): 7.2 (1H, d, J=8 Hz), 6.6 (1H, d, J=8 Hz), 2.2 (3H, s), 1.7 (6H, s), 1.6 (9H, s).

Step 4

Preparation of t-butyl 7-bromomethyl-2,2-dimethylbenzodioxol-4-carboxylate.

To a solution of the product obtained in Step 3 (7.2 g) in carbon tetrachloride (40 ml) were added N-bromosuccinimide (4.85 g) and benzoyl peroxide (25 mg), and the mixture was refluxed for 70 minutes. The reaction mixture was then cooled to room temperature and insoluble matter was filtered off. The filtrate was washed once with water (50 ml), once with brine (50 ml), and then concentrated under reduced pressure. The residue was purified by silica gel column chromatography to give 9.4 g of the objective compound.

IR (neat; cm$^{-1}$): 1717, 1448, 1308, 1220, 1203, 1102.

NMR (CDCl$_3$; ppm): 7.3 (1H, d, J=8 Hz), 6.8 (1H, d, J=8 Hz) 4.4 (2H, s), 1.8 (6H, s), 1.6 (9H, s).

Step 5

Preparation of t-butyl 2,2-dimethyl-7-(N-phthaloyloxymethyl)benzodioxol-4-carboxylate.

To a solution of the product obtained in Step 4 (9.4 g) in acetonitrile (60 ml) was added dropwise a solution of N-hydroxyphthalimide (4.0 g) and triethylamine (3.4 ml) in acetonitrile (40 ml) at room temperature. After stirring for 1 hour, a solution of N-hydroxyphthalimide (0.4 g) and triethylamine (0.34 ml) in acetonitrile (4 ml) was added dropwise to the reaction mixture. After stirring for further 1 hour, the reaction mixture was poured into ice water (200 ml) and extracted twice with ethyl acetate (150 ml, and then 100 ml). The organic layer was washed thrice with saturated aqueous solution of sodium hydrogen carbonate (100 ml each), once with aqueous solution of citric acid (1N, 150 ml) and with brine (100 ml), then dried over anhydrous sodium sulfate. The dried solution was concentrated under reduced pressure, and the residue was crystallized with n-hexane (150 ml) to give 7.8 g of the objective compound.

IR (KBr; cm$^{-1}$): 1729, 1710, 1456, 1307, 1152, 1072.

NMR (CDCl$_3$; ppm): 7.8 (4H, m), 7.3 (1H, d, J=8 Hz), 6.9 (1H, d, J=8 Hz), 5.2 (2H, s), 1.6 (9H, s), 1.5 (6H, s).

Step 6

Preparation of t-butyl 7-aminooxymethyl-2,2-dimethylbenzodioxol-4-carboxylate.

To a solution of the product obtained in Step 5 (7.8 g) in methylene chloride (130 ml) was added a solution of methylhydrazine (1.01 g) in methylene chloride (20 ml) at −30° C., and the mixture was stirred for 1 hour under ice cooling. After filtrating insoluble matter off, the filtrate was concentrated under reduced pressure. The residue was purified by silica gel column chromatography to give 5.4 g of the objective compound.

IR (neat; cm$^{-1}$): 1710, 1444, 1368, 1306, 1205.

NMR (CDCl$_3$; ppm): 7.3 (1H, d, J=8 Hz), 6.8 (1H, d, J=8 Hz), 5.3 (2H, brs), 4.7 (2H, s) 1.7 (6H, s), 1.6 (9H, s).

Step 7

Preparation 2-(2-amino-4-thiazolyl)-2-[Z-[(4-t-butoxycarbonyl-2,2-dimethylbenzodioxol-7-yl)methyl]oxyimino]acetic acid.

To a solution of the product obtained in Step 6 (5.4 g) in N,N-dimethylformamide (25 ml) was added (2-aminothiazol-4-yl)glyoxylic acid (3.2 g), and the mixture was stirred at room temperature for 60 minutes. The reaction mixture was poured into ice-water (250 ml), and precipitated crystals were separated by filtration. The crystals were dissolved in ethyl acetate (500 ml), washed twice with water (150 ml each), twice with brine (150 ml each) and dried over anhydrous sodium sulfate. The dried solution was concentrated under reduced pressure, and the residue was crystallized with ether (50 ml) and hexane (100 ml) to give 6.7 g of the objective compound.

IR (KBr; cm$^{-1}$): 1710, 1625, 1445, 1369, 1309, 1207.

NMR (DMSO-d$_6$; ppm): 7.2 (2H, brs), 7.2 (1H, d, J=8 Hz), 6.9 (1H, d, J=8 Hz), 6.8 (1H, s), 5.1 (2H, s), 1.7 (6H, s), 1.5 (9H, s).

Step 8

Preparation of (6R,7R)-7-[2-(2-amino-4-thiazolyl)-2-[Z-[(4-t-butoxycarbonyl-2,2-dimethylbenzodioxol-7-yl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To a suspension of the product obtained in Step 7 (0.98 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (1.5 g) in methylene chloride (20 ml) were added pyridine (0.17 ml) and a solution of phosphorous oxychloride (0.2 ml) in methylene chloride (1 ml) at −10° C., and the mixture was stirred at −10° C. for 1 hour. The product obtained in Step 7 (0.1 g) was added to the reaction mixture, and the solution was stirred for further 1 hour at 10° C. The reaction mixture was then poured into precooled aqueous hydrochloric acid (1 N, 100 ml), and extracted once with ethyl acetate (300 ml). The organic layer was washed twice with aqueous hydrochloric acid (1 N, 100 ml each), twice with saturated aqueous solution of sodium hydrogen carbonate (100 ml each) twice with brine (100 ml each) and dried over anhydrous sodium sulfate. The dried solution was concentrated under reduced pressure. The residue was purified by silica gel column chromatography to give 1.4 g of the objective compound.

IR (KBr; cm$^{-1}$): 1792, 1718, 1508, 1448, 1205, 1182.

NMR (DMSO-d$_6$; ppm): 9.8 (1H, d, J=8 Hz), 7.6–6.9 (27H, m), 6.8 (1H, s), 5.9 (1H, dd, J=8, 5 Hz), 5.3 (1H, d, J=5 Hz), 5.1 (2H, s), 4.3 (2H, s), 3.7 (2H, ABq), 2.6 (3H, s), 1.7 (6H, s), 1.5 (9H, s).

Step 9

Preparation of (6R,7R)-7-[2-(2-amino-4-thiazolyl)-2-[Z-[(4-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a suspension of the product of Step 8 (1.4 g) in anisole (1 ml) was added trifluoroacetic acid (5 ml) under ice cooling, and the resultant mixture was stirred at room temperature for 4 hours. Ether (100 ml) was added to the mixture, and precipitated crystals were separated by filtration. These crystals were suspended in anisole (2 ml), and trifluoroacetic acid (5 ml) was added under ice cooling, and the mixture stirred at room temperature for 6.5 hours. The reaction mixture was then poured into ether (100 ml). The precipitated crystals were suspended in water (4 ml) and the pH of the suspension was adjusted to 8.0 with sodium hydrogen carbonate. The resultant solution was applied to a Diaion HP-20 column and eluted with water. Fractions containing the objective compound were collected and concentrated under reduced pressure to ca. 1 ml. The concentrate was crystallized by pouring into ethanol (20 ml) to give 0.28 g of the objective compound.

IR (KBr; cm$^{-1}$): 1762, 1598, 1514, 1405, 1356, 1313.

NMR (D$_2$O; ppm): 7.3 (1H, d, J=8 Hz), 7.2 (1H, s), 7.0 (1H, s), 6.9 (1H, d, J=8 Hz), 5.7 (1H, d, J=5 Hz), 5.3 (2H, s), 5.1 (1H, d, J=5 Hz), 4.3 (2H, ABq), 3.5 (2H, ABq), 2.6 (3H, s).

EXAMPLE 8

Preparation of (6R,7R)-7-[2-(2-amino-4-thiazolyl)-2-[Z-[(4-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

Step 1

Preparation of ethyl 2-(2-amino-4-thiazolyl)-2-[Z-[(4-t-butoxycarbonyl-2,2-dimethylbenzodioxol-7-yl)methyl]oxyimino]acetate.

To a solution of ethyl 2-(2-amino-4-thiazolyl)-2-(Z-hydroxyimino)acetate (1 g) in dry N,N-dimethylformamide (10 ml) was added sodium hydride (60% dispersion in mineral oil; 200 mg) under ice cooling, and the mixture was stirred for 15 minutes. To the mixture was added dropwise a solution of the product obtained in Step 4 of Example 7 (1.9 g) in N,N-dimethylformamide (10 ml). The mixture was stirred under ice cooling for 1.5 hours. The reaction mixture was then poured into an ice-cooled mixture of aqueous hydrochloric acid (1 N, 200 ml) and ethyl acetate (200 ml, and stirred vigorously. The organic layer was separated and washed once with saturated aqueous solution of sodium hydrogen carbonate (100 ml) and thrice with brine (100 ml each). The washed solution was dried over anhydrous sodium sulfate. The dried solution was concentrated under reduced pressure, and the residue was crystallized with hexane (50 ml) to give 1.87 g of the objective compound.

NMR (CDCl$_3$; ppm): 7.3 (1H, d, J=8 Hz), 6.9 (1H, d, J=8 Hz), 6.7 (1H, s), 5.7 (2H, bs), 5.3 (2H, s), 4.4 (2H, q, J=7 Hz), 1.7 (6H, s), 1.6 (9H, s), 1.4 (3H, t, J=7 Hz).

Step 2

Preparation 2-(2-amino-4-thiazolyl)-2-[Z-[(4-t-butoxycarbonyl-2,2-dimethylbenzodioxol-7-yl)methyl]oxyimino]acetic acid.

To a suspension of the product of Step 1 (1 g) in ethanol (6 ml) was added an aqueous solution of sodium hydroxide (conc. 2N, 2.1 ml), and the mixture was stirred for 2 hours at room temperature, then for 1 hour at 63° C. The reaction mixture was concentrated under reduced pressure, and water (20 ml) was added to the residue. The mixture was acidified with aqueous hydrochloric acid (1N) to pH 3, then extracted with ethyl acetate (50 ml). The extract was washed twice with brine (30 ml each) and dried over anhydrous sodium sulfate. The dried solution was concentrated under reduced pressure, and the residue was crystallized with ether-hexane (1:1, 30 ml) to give 860 mg of the objective compound.

IR (KBr; cm$^{-1}$): 1710, 1625, 1445, 1369, 1309, 1207.

NMR (DMSO-d$_6$; ppm): 7.2 (2H, bs), 7.2 (1H, d, J=8 Hz), 6.9 (1H, d, J=8 Hz), 6.8 (1H, s), 5.1 (2H, s), 1.7 (6H, s), 1.5 (9H, s). These data are in complete agreement with those of Step 7 of Example 7.

Step 3

Preparation of (6R,7R)-7-[2-(2-amino-4-thiazolyl)-2-[Z-[(4-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The compound of the title given above was prepared from the product of Step 2, according to the methods of Steps 8 and 9 of Example 1.

IR (KBr; cm$^{-1}$): 1762, 1598, 1514, 1405, 1356, 1313.

NMR (D$_2$O; ppm): 7.3 (1H, d, J=8 Hz), 7.2 (1H, s), 7.0 (1H, s), 6.9 (1H, d, J=8 Hz), 5.7 (1H, d, J=5 Hz), 5.3 (2H, s), 5.1 (1H, d, J=5 Hz), 4.3 (2H, ABq), 3.5 (2H, ABq), 2.6 (3H, s). These data are in complete agreement with those of Step 9 of Example 7.

According to the method described in Example 7, compounds of Examples 9 and 10 described below, were prepared. According to the method described in Example 8, compounds of Examples 11 and 12, described below, were prepared.

EXAMPLE 9

(6R,7R)-7-[2-(2-amino-4-thiazolyl)-2-[Z--[(4-carboxy-2,3-dihydroxyphenyl)methyl]oxyimino]acetamido]-3-[(5-methyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1596, 1512, 1401, 1352.

NMR (D$_2$O; ppm): 8.5 (1H, s), 7.3 (1H, d, J=8 Hz), 7.2 (1H, s), 7.0 (1H, s), 6.9 (1H, s, J=8 Hz), 5.7 (1H,d, J=5 Hz), 5.1 (2H, s), 5.0 (1H, d, J=5 Hz), 4.3 (2H, ABq), 3.5 (2H, ABq), 2.6 (3H, s).

EXAMPLE 10

(6R,7R)-7-[2-(2-amino-4-thiazolyl)-2-[Z-[-(4-carboxy-2,3-dihydroxyphenyl)methyl]oxyimino]acetamido]-3-[(5-carboxy-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1600, 1513, 1402.

NMR (D$_2$O; ppm): 8.5 (1H, s), 7.3 (1H, d, J=8 Hz), 7.2 (1H, s), 7.0 (1H, s), 6.9 (1H, d, J=8 Hz), 5.7 (1H, d, J=5 Hz), 5.3 (2H, s), 5.1 (1H, d, J=5 Hz), 4.3 (2H, ABq), 3.5 (2H, ABq).

EXAMPLE 11

(6R,7R)-7-[2-(2-amino-4-thiazolyl)-2-[Z-[(4-carboxy-2,3-dihydroxyphenyl)methyl]oxyimino]acetamido]-3-[(5-carboxymethyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1598, 1509, 1398.

NMR (D$_2$O; ppm): 8.5 (1H, s), 7.3 (1H, d, J=8 Hz), 7.2 (1H, s), 7.0 (1H, s), 6.9 (1H, d, J=8 Hz), 5.7 (1H, d, J=5 Hz), 5.3 (2H, s), 5.1 (1H, d, J=5 Hz), 4.3 (2H, ABq), 3.5 (2H, ABq), 2.6 (2H,s).

EXAMPLE 12

(6R,7R)-7-[2-(2-amino-4-thiazolyl)-2-[Z-[(4-carboxy-2,3-dihydroxyphenyl)methyl]oxyimino]acetamido]-3-[(2-sulfo-5-methyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1595, 1515, 1402.

NMR (D$_2$O; ppm): 7.3 (1H, d, J=8 Hz), 7.2 (1H, s), 7.0 (1H, s), 6.9 (1H, d, J=8 Hz), 5.7 (1H, d, J=5 Hz), 5.3 (2H, s), 5.1 (1H, d, J=5 Hz), 4.3 (2H, ABq), 3.5 (2H, ABq), 2.6 (3H, s).

EXAMPLE 13

Preparation of (6R,7R)-7-[2-(2-amino-4-thiazolyl)-2-[Z-[(6-carboxy-2,3-dihydroxyphenyl)methyl]oxyimino]acetamido]-3-[(2-carboxy-5-methyl-s-triazolo[1,5-a]pyrimidin-7-yl]thiomethyl]-8-oxo-5-thia-1-azabicyclo[4.2.0]oct-2-ene-2-carboxylic acid (Compound 1).

Step 1

Preparation of 5-acethyl-2,2,4-trimethylbenzodioxol

To a solution of 2,2,4-trimethylbenzodioxol (100 g) in acetic anhydride (500 ml) was added zinc chloride (50 g) under ice cooling, and the solution was stirred 0° C. for 2 hours, then at room temperature for 2.5 hours. The reaction mixture was concentrated under reduced pressure, and poured into ice-water (400 ml) followed by extraction with ether (500 ml). The aqueous layer was extracted with ether (200 ml). The combined organic layer was washed four times with water (150 ml each), twice with saturated aqueous solution of sodium hydrogen carbonate (150 ml each) and twice with brine (150 ml each). The washed solution was dried over anhydrous sodium sulfate. The dried solution was concentrated under reduced pressure, and the residue was purified by silica gel column chromatography to give 27.5 g of the objective compound.

IR (neat; cm$^{-1}$): 1675, 1596, 1478, 1265, 1228.

NMR (CDCl$_3$; ppm): 7.4 (1H, d, J=8 Hz), 6.6 (1H, d, J=8 Hz), 2.5 (3H, s), 2.4 (3H, s), 1.7 (6H,s).

Step 2

Preparation of 2,2,4-trimethylbenzodioxol-5-carboxylic acid.

To a suspension of calicum hypochlorite (79 g) in water (315 ml), warmed to 60° C., was added in solution of sodium carbonate (55 g) and sodium hydroxide (16 g) in water (159 ml). After stirring for 10 minutes, the solution was filtered. To the filtrate, warmed to 55° C., was added the compound (27.5 g) obtained in step 1. The reaction mixture was stirred at 70° C. for 1.5 hours, and then cooled with ice. To this solution was added a solution of sodium bisulfite (16 g) in water (30 ml) followed by stirring for 1 hour. After extracting with ether (100 ml), the aqueous layer was acidified to pH 2 with aqueous hydrochloric acid. The precipitated solid was separated by filtration and washed with water (100 ml), and dried to give 11.4 g of the objective compound.

IR (KBr; cm$^{-1}$): 2991, 1676, 1467, 1275, 1224.

NMR (CDCl$_3$; ppm): 7.7 (1H, d, J=8 Hz), 6.6 (1H, d, J=8 Hz), 2.5 (3H, s) 1.7 (6H, s).

Step 3

Preparation of t-butyl 2,2,4-trimethylbenzo dioxol-5-carboxylate.

To a suspension of the product obtained in Step 2 (11.4 g) in benzene (100 ml) were added thionyl chloride (16 ml) and N,N-dimethylformamide (5 drops). After stirring for 1 hour at room temperature, the solvent was removed under reduced pressure. The residue was dissolved in methylene chloride (50 ml), and the solution was added dropwise to an ice-cooled mixture of t-butanol (52 ml) and pyridine (26.7 ml). After stirring for 15 hours at room temperature, the solvent was removed under reduced pressure. The residue was dissolved in ether (300 ml), and the ether solution was washed twice with water (150 ml each), twice with aqueous hydrochloric acid (1 N, 150 ml each), twice with saturated aqueous solution of sodium hydrogen carbonate (150 ml each) and once with brine (150 ml), then dried over anhydrous sodium sulfate. The dried solution was concentrated under reduced pressure, and the residue was purified by silica gel column chromatography to give 14.5 g of objective compound.

IR (neat; cm$^{-1}$): 1708, 1475, 1464, 1289, 1270, 1169.

NMR (CDCl$_3$; ppm): 7.5 (1H, d, J=8 Hz), 6.6 (1H, d, J=8 Hz), 2.4 (3H, s), 1.7 (6H, s), 1.6 (9H, s).

Step 4

Preparation of t-butyl 4-bromomethyl-2,2-dimethylbenzodioxol-5-carboxylate.

To a solution of the product obtained in Step 3 (13.5 g) in carbon tetrachloride (70 ml) were added N-bromosuccinimide (8.7 g) and benzoyl peroxide (30 mg), and the mixture was refluxed for 70 minutes. The reaction mixture was then cooled to room temperature and insoluble matter was removed by filtration. The filtrate was washed once with saturated aqueous solution of sodium hydrogen carbonate (50 ml), once with brine (50 ml) and dried over anhydrous sodium sulfate. The dried solution was concentrated under reduced pressure to give 17.0 g of the objective compound.

IR (neat; cm$^{-1}$): 1708, 1458, 1295, 1268, 1168.

NMR (CDCl$_3$; ppm): 7.5 (1H, d, J=8 Hz), 6.7 (1H, d, J=8 Hz), 4.9 (2H, s), 1.7 (6H, s), 1.6 (9H, s).

Step 5

Preparation of t-butyl 2,2-dimethyl-4-(N-phthaloyloxymethyl)benzodioxol-5-carboxylate.

To a solution of the product obtained in Step 4 (17.0 g) in acetonitrile (150 ml) were added dropwise a solution of N-hydroxyphthalimide (8.1 g) and a solution triethylamine (6.9 ml) in acetonitrile (50 ml) at room temperature, and the mixture was stirred for 1.5 hours. The reaction mixture was then poured into ice water (300 ml) and extracted with ether (once with 400 ml, twice with 200 ml). The combined organic layer was washed five times with aqueous solution of sodium hydrogen carbonate (150 ml each), and once with brine (150 ml). The washed solution was dried over anhydrous sodium sulfate. The dried solution was concentrated under reduced pressure, and the residue was crystallized with hexane to give 15.5 g of the objective compound.

IR (KBr; cm$^{-1}$): 1790, 1727, 1695, 1300, 1258.

NMR (CDCl$_3$; ppm): 7.7 (4H, m), 7.6 (1H, d, J=8 Hz), 6.7 (1H, d, J=8 Hz), 5.6 (2H, s), 1.6 (9H, s), 1.4 (6H, s).

Step 6

Preparation of t-butyl 4-aminooxymethyl-2,2-dimethylbenzodioxol-5-carboxylate.

To a solution of the product obtained in Step 5 (5.0 g) in methylene chloride (90 ml) was added a solution of methylhydrazine (0.6 g) in methylene chloride (10 ml) at −30° C., and the mixture was stirred for 1 hour under ice cooling. To the reaction mixture was added methylhydrazine (0.2 g), and the mixture was stirred for further 30 minutes. Insoluble matter was filtered off, and the filtrate was concentrated under reduced pressure. The residue was purified by silica gel column chromatography to give 3.3 g of the objective compound.

NMR (CDCl$_3$; ppm): 7.4 (1H, d, J=8 Hz), 6.8 (1H, d, J=8 Hz), 5.0 (2H, s), 1.7 (6H, s), 1.6 (9H, s).

Step 7

Preparation 2-(2-amino-4-thiazolyl)-2-[Z-[(5-t-butoxycarbonyl-2,2-dimethylbenzodioxol-4-yl)methyl]oxyimino]acetic acid.

To a solution of the product obtained in Step 6 (3.2 g) in N,N-dimethylformamide (20 ml) was added (2-aminothiazol-4-yl)glyoxylic acid (1.7 g), and the mixture was stirred at room temperature for 90 minutes. The reaction mixture was concentrated under reduced pressure, and the residue was dissolved in ethyl acetate (120 ml). The solution was washed four times with water (50 ml each), once with brine (50 ml), and dried over anhydrous sodium sulfate. The dried solution was concentrated under reduced pressure, and the residue was crystallized with ether and hexane (1:1) to give 4.0 g of the objective compound.

IR (KBr; cm$^{-1}$): 1625, 1459, 1297, 1263, 1161.

NMR (DMSO-d$_6$; ppm): 7.4 (1H, d, J=8 Hz), 7.2 (2H, brs), 6.9 (1H, d, J=8 Hz), 6.8 (1H, s), 5.3 (2H, s), 1.7 (6H, s), 1.5 (9H, s).

Step 8

Preparation of (6R,7R)-7-[2-(2-amino-4-thiazolyl)-2-[Z-[(5-t-butoxycarbonyl-2,2-dimethylbenzodioxol-4-yl)methyl]oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To a solution of the product obtained in Step 7 (3.5 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (5.0 g) in methylene chloride (120 ml) was added N,N-dicyclohexylcarbodiimide (1.9 g), and the mixture was stirred for 20 hours at room temperature. The reaction mixture was then concentrated under reduced pressure, and the residue was dissolved in acetone (50 ml) and insoluble matter was filtered off. The filtrate was purified by silica gel column chromatography to give 3.5 g of the objective compound.

IR (KBr; cm$^{-1}$): 1792, 1508, 1458, 1257, 1222, 1203.

NMR (DMSO-d$_6$; ppm): 9.4 (1H, d, J=8 Hz), 7.5–6.7 (28H, m), 5.8 (1H, dd, J=8, 5 Hz), 5.4 (2H, s), 5.2 (1H, d, J=5 Hz), 4.3 (2H, s), 3.6 (2H, ABq), 2.6 (3H, s), 1.6 (6H, s), 1.5 (9H, s).

Step 9

Preparation of (6R,7R)-7-[2-(2-amino-4-thiazolyl)-2-[Z-[(6-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a suspension of the product of Step 8 (3.4 g) in dichloroethane (2.3 ml) was added anisole (2.3 ml). To the mixture was added trifluoroacetic acid (9 ml) under ice cooling, and the resultant mixture was stirred for 1 hour at room temperature. The reaction mixture was then poured into ether (100 ml). The precipitated crystals were separated by filtration and added to trifluoroacetic acid (20 ml) under ice cooling. The resultant mixture was stirred at room temperature for 20 hours, and poured into ether (100 ml). The precipitated crystals were separated by filtration, suspended in water (30 ml) and the pH of the suspension was adjusted to 8.0 with sodium hydrogen carbonate. The resultant solution was applied to a Diaion HP-20 column and eluted with water. Fractions containing the objective compound were collected and concentrated to ca. 5 ml under reduced pressure. The concentrate was crystallized by pouring into ethanol (100 ml) to give 0.5 g of the objective compound.

IR (KBr; cm$^{-1}$): 1762, 1598, 1514, 1395, 1314.

NMR (D$_2$O; ppm): 7.3 (1H, s), 7.1 (1H, s), 7.0 (1H, d, J=8 Hz), 6.9 (1H, d, J=8 Hz), 5.7 (1H, d, J=5 Hz), 5.6 (2H, s), 5.1 (1H, d, J=5 Hz), 4.4 (2H, ABq), 3.4 (2H, ABq), 2.7 (3H, s).

EXAMPLE 14

Preparation of (6R,7R)-7-[2-(2-amino-4-thiazolyl)-2-[Z-[(6-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

Step 1

Preparation of ethyl 2-(2-amino-4-thiazolyl)-2-[Z-[(5-t-butoxycarbonyl-2,2-dimethylbenzodioxol-4-yl)methyl]oxyimino]acetate.

To a solution of ethyl 2-(2-amino-4-thiazolyl)-2-(Z-hydroxyimino)acetate (1 g) in dry N,N-dimethylformamide (10 ml) was added sodium hydride (60% dispersion in mineral oil; 200 mg) under ice cooling, and the mixture was stirred for 15 minutes. To the mixture was added dropwise a solution of the product obtained in Step 4 of Example 13 (1.9 g) in N,N-dimethylformamide (10 ml). The mixture was stirred under ice cooling for 1.5 hours. The reaction mixture was then poured into an ice-cooled mixture of conc. hydrochloric acid and ethyl acetate (200 ml each) and stirred thoroughly. The organic layer was separated and washed once with saturated aqueous solution of sodium hydrogen carbonate (100 ml) and thrice with brine (100 ml each). The washed solution was dried over anhydrous sodium sulfate. The dried solution was concentrated under reduced pressure, and the residue was crystallized with hexane (50 ml) to give 1.78 g of the objective compound.

NMR (CDCl$_3$; ppm): 7.5 (1H, d, J=8 Hz), 6.67 (1H, s), 6.65 (1H, d, J=8 Hz), 5.7 (2H, bs), 5.6 (2H, s), 4.4

(2H, q, J=7 Hz), 1.7 (6H, s), 1.6 (9H, s), 1.4 (3H, t, J=7 Hz).

Step 2

Preparation 2-(2-amino-4-thiazolyl)-2-[Z-[(5-t-butoxycarbonyl-2,2-dimethylbenzodioxol-4-yl)methyl]oxyimino]acetic acid.

To a suspension of the product of Step 1 (1 g) in ethanol (6 ml) was added an aqueous solution of sodium hydroxide (2N, 2.1 ml), and the mixture was stirred for 2 hours at room temperature, then for 1 hour at 63° C. The reaction mixture was concentrated under reduced pressure, and water (20 ml) was added to the residue. The mixture was acidified with aqueous hydrochloric acid (1N) to pH 3, then extracted with ethyl acetate (50 ml). The extract was washed twice with brine (30 ml each) and dried over anhydrous sodium sulfate. The dried solution was concentrated under reduced pressure, and the residue was crystallized with ether-hexane (1:1, 30 ml) to give 840 mg of the objective compound.

IR (KBr; cm$^{-1}$): 1625, 1459, 1297, 1263, 1161.

NMR (DMSO-$d_6$; ppm): 7.4 (1H, d, J=8 Hz), 7.2 (2H, bs), 6.9 (1H, d, J=8 Hz), 6.8 (1H, s), 5.3 (2H, s), 1.7 (6H, s), 1.5 (9H, s). These data are in complete agreement with those of Step 7 of Example 13.

Step 3

Preparation of (6R,7R)-7-[2-(2-amino-4-thiazolyl)-2-[Z-[(6-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The compound of the title given above was prepared from the product of Step 2, according to the methods of Steps 8 and 9 of Example 13.

IR (KBr, cm$^{-1}$): 1762, 1598, 1514, 1395, 1314.

NMR (D$_2$O; ppm): 7.3 (1H, s), 7.1 (1H, s), 7.0 (1H, d, J=8 Hz), 6.9 (1H, d, J=8 Hz), 5.7(1H, d, J=5 Hz), 5.6 (2H, s), 5.1 (1H, d, J=5 Hz), 4.4 (2H, ABq), 3.4 (2H, ABq), 2.7 (3H, s).

These data are in complete agreement with those of Step 9 of Example 13.

According to the method described in Example 13, compounds of Examples 15 and 16, described below, were prepared. According to the method described in Example 14, compounds of Examples 17 and 18, described below, were prepared.

EXAMPLE 15

(6R,7R)-7-[2-(2-amino-4-thiazolyl)-2-[Z--[(6-carboxy-2,3-dihydroxyphenyl)methyl]oxyimino]acetamido]-3-[(5-methyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1596, 1514, 1398.

NMR (D$_2$O; ppm): 8.5 (1H, s), 7.3 (1H, s), 7.1 (1H, s), 7.0 (1H, d, J=8 Hz), 6.9 (1H, d, J=8 Hz), 5.7 (1H, d, J=5 Hz), 5.6 (2H, s), 5.1 (1H, d, J=5 Hz) 4.4 (2H, ABq), 3.4 (2H, ABq), 2.6 (3H, s).

EXAMPLE 16

(6R,7R)-7-[2-(2-amino-4-thiazolyl)-2-[Z-[-(6-carboxy-2,3-dihydroxyphenyl)methyl]oxyimino]acetamido]-3-[(5-carboxy-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1598, 1533, 1395.

NMR (D$_2$O; ppm): 8.5 (1H, s), 7.4 (1H, s), 7.1 (1H, s), 7.0 (1H, d, J=8 Hz), 6.9 (1H, d, J=8 Hz), 5.7 (1H, d, J=5 Hz), 5.6 (2H, s), 5.1 (1H, d, J=5 Hz), 4.4 (2H, ABq), 3.4 (2H, ABq).

EXAMPLE 17

(6R,7R)-7-[2-(2-amino-4-thiazolyl)-2-[Z-[(6-carboxy-2,3-dihydroxyphenyl)methyl]oxyimino]acetamido]-3-[(5-carboxymethyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1594, 1514, 1392.

NMR (D$_2$O; ppm): 8.5 (1H, s), 7.3 (1H, s), 7.1 (1H, s), 7.0 (1H, d, J=8 Hz), 6.9 (1H, d, J=8 Hz), 5.7 (1H, d, J=5 Hz), 5.6 (2H, s), 5.1 (1H, d, J=5 Hz), 4.4 (2H, ABq), 3.4 (2H, ABq), 2.6 (2H, s).

EXAMPLE 18

(6R,7R)-7-[2-(2-amino-4-thiazolyl)-2-[Z-[(6-carboxy-2,3-dihydroxyphenyl)methyl]oxyimino]acetamido]-3-[(2-sulfo-5-methyl-s-triazolo[1,5-a]pyrimidin-7-yl)thiomethyl]-8-oxo-5-thia-1-azabicyclo[4.2.0oct-2-ene-2-carboxylic acid IR (KBr; cm$^{-1}$): 1762, 1596, 1510, 1397, 1368.

NMR (D$_2$O; ppm): 7.3 (1H, s), 7.1 (1H, s), 7.0 (1H, d, J=8 Hz), 6.9 (1H, d, J=8 Hz), 5.7 (1H, d, J=5 Hz), 5.6 (2H, s), 5.1 (1H, d, J=5 Hz), 4.4 (2H, ABq), 3.4 (2H, ABq), 2.6 (3H, s).

EXAMPLE 19

Preparation of (6R,7R)-7-[2-(2-amino-4-thiazolyl)-2-[Z-[(2-carboxy-3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 4).

Step 1

Preparation of methyl 2,2,5-trimethylbenzodioxol-4-carboxylate.

To a solution of methyl 2,3-dihydroxy-6-methyl benzoate (17 g) in acetone (380 ml) was added phosphorous pentoxide (10 times, 20 g each, interval 30 minutes) while stirring vigorously. After the addition, the reaction mixture was stirred for further 30 minutes, and decanted. The decanted solution was concentrated under reduced pressure. The residue was dissolved in ethyl acetate (200 ml), and the solution was washed once with saturated aqueous solution of sodium hydrogen carbonate (70 ml), once with brine (70 ml) and dried over anhydrous sodium sulfate. The dried solution was concentrated under reduced pressure. To the residue was added n-hexane (150 ml), and precipitated matter was filtered off. The filtrate was washed thrice with aqueous solution of sodium hydroxide (1N, 50 ml each), once with brine (50 ml) and dried over anhydrous sodium sulfate. The dried solution was concentrated under reduced pressure and resultant residue was purified by silica gel column chromatography to give 6.9 g of the objective compound.

IR (neat; cm$^{-1}$): 1725, 1459, 1288, 1242, 1100.

NMR (CDCl$_3$; ppm): 6.7 (1H, d, J=8 Hz), 6,6 (1H, d, J=8 Hz), 3.9 (3H, s), 2.4 (3H, s), 1.7 (6H, s).

Step 2

Preparation of 2,2,5-trimethylbenzodioxol-4-carboxylic acid.

To a suspension of the compound (6.8 g) obtained in step 1 in ethanol (100 ml) was added aqueous solution of potassium hydroxide (3N, 20 ml). After refluxing for 35 minutes, the reaction mixture was concentrated to ca. 30 ml, and dissolved in water (150 ml), followed by washing with ether (50 ml). The aqueous layer was acidified to pH 3 with aqueous hydrochloric acid (4N) and extracted with ethyl acetate (once with 150 ml, twice with 70 ml). The extracts were combined and washed twice with brine (70 ml each), and dried over anhydrous sodium sulfate. The dried solution was concentrated under reduced pressure. The residue was washed with n-hexane (50 ml) to give 6.0 g of the objective compound.

IR (KBr; cm$^{-1}$) 1686, 1479, 1450, 1303, 1236.

NMR (CDCl$_3$, ppm): 10.5 (1H, brs), 6.8 (1H, d, J=8 Hz), 6.6 (1H, d, J=8 Hz), 2.5 (3H, s), 1.7 (6H, s).

Step 3

Preparation of t-butyl 2,2,5-trimethylbenzo dioxol-4-carboxylate.

To a suspension of the product obtained in Step 2 (6.0 g) in benzene (50 ml) were added thionyl chloride (8 ml) and N,N-dimethylformamide (3 drops). After stirring for 1 hour at room temperature, the solvent was removed under reduced pressure. The residue was dissolved in methylene chloride (25 ml), and added dropwise to an ice-cooled mixture of t-butanol (25 ml) and pyridine (13 ml). After stirring at room temperature for 39 hours, the solvent was removed under reduced pressure. The residue was dissolved in ether (300 ml), and the solution was washed once with water (150 ml), thrice with aqueous hydrochloric acid (1N, 100 ml each), twice with saturated aqueous solution of sodium hydrogen carbonate (100 ml each) and once with brine (100 ml). After drying over anhydrous sodium sulfate, the solution was concentrated under reduced pressure and the resultant residue was purified by silica gel column chromatography to give 6.0 g of the objective compound.

IR (neat; cm$^{-1}$): 1717, 1459, 1296, 1245, 1101.

NMR (CDCl$_3$; ppm): 6.7 (1H, d, J=8 Hz), 6.5 (1H, d, J=8 Hz), 2.4 (3H, s), 1.7 (6H, s), 1.6 (9H, s).

Step 4

Preparation of t-butyl 5-bromomethyl-2,2-dimethylbenzodioxol-4-carboxylate.

To a solution of the product obtained in Step 3 (6.0 g) in carbon tetrachloride (50 ml) were added N-bromosuccinimide (4.0 g) and benzoyl peroxide (14 mg), and the mixture was refluxed for 95 minutes. The reaction mixture was then cooled to room temperature and insoluble matter was removed by filtration. The filtrate was washed once with water (30 ml), once with saturated aqueous solution of sodium hydrogen carbonate (30 ml) and once with brine (30 ml), then dried over anhydrous magnesium sulfate. The dried solution was concentrated under reduced pressure to give 7.7 g of the objective compound.

IR (neat; cm$^{-1}$): 1716, 1457, 1306, 1246, 1214.

NMR (CDCl$_3$; ppm): 6.8 (1H, d, J=8 Hz), 6.7 (1H, d, J=8 Hz), 4.8 (2H, s), 1.7 (6H, s), 1.6 (9H, s).

Step 5

Preparation of t-butyl 2,2-dimethyl-5-(N-phthaloyloxymethyl)benzodioxol-4-carboxylate.

To a solution of the product obtained in Step 4 (7.7 g) in acetonitrile (30 ml) was added dropwise a solution of N-hydroxyphthalimide (3.66 g) and triethylamine (3.12 ml) in acetonitrile (70 ml) at room temperature over 80 minutes period. The reaction mixture was poured into ice water (250 ml) and extracted twice with ether (450 ml each). The organic layer was washed once with aqueous solution of citric acid (1 N, 150 ml), twice with saturated aqueous solution of sodium hydrogen carbonate (150 ml each) and once with brine (150 ml). The washed solution was dried over anhydrous magnesium sulfate. The dried solution was concentrated under reduced pressure to give 7.6 g of the objective compound.

IR (KBr; cm$^{-1}$): 1745, 1706, 1478, 1451, 1304, 1234, 978.

NMR (CDCl$_3$; ppm): 7.7 (4H, m), 7.0 (1H, d, J=8 Hz), 6.7 (1H, d, J=8 Hz), 5.4 (2H, s), 1.7 (6H, s), 1.6 (9H, s).

Step 6

Preparation of t-butyl 5-aminooxymethyl-2,2-dimethylbenzodioxol-4-carboxylate.

To a solution of the product obtained in Step 5 (7.6 g) in methylene chloride (80 ml) was added a solution of methylhydrazine (902 mg) in methylene chloride (20 ml) at $-70°$ C., and the mixture was stirred for 50 minutes under ice cooling. Insoluble matter was filtered off, and the filtrate was concentrated under reduced pressure. The residue was purified by silica gel column chromatography to give 4.6 g of the objective compound.

IR (neat; cm$^{-1}$): 1718, 1459, 1298, 1247.

NMR (CDCl$_3$, ppm): 6.8 (1H, d, J=8 Hz), 6.7 (1H, d, J=8 Hz), 4.8 (2H, s), 4.1 (2H, brs) 1.7 (6H, s), 1.6 (9H, s).

Step 7

Preparation 2-(2-amino-4-thiazolyl)-2-[Z-[(4-t-butoxycarbonyl-2,2-dimethylbenzodioxol-5-yl)methyl]oxyimino]acetic acid.

To a solution of the product obtained in Step 6 (4.6 g) in N,N-dimethylformamide (45 ml) was added (2-aminothiazol-4-yl)glyoxylic acid (2.68 g), and the mixture was stirred at room temperature for 65 minutes. The reaction mixture was poured into ice-water (200 ml), and precipitated crystals were separated by filtration. The crystals were washed with water and dried at room temperature to give 5.9 g of the objective compound.

IR (KBr; cm$^{-1}$): 1717, 1597, 1473, 1456, 1247, 999.

NMR (DMSO-d$_6$; ppm): 7.2 (2H, brs), 6.9 (2H, s), 6.8 (1H, s), 5.2 (2H, s), 1.7 (6H, s), 1.5 (9H, s).

Step 8

Preparation of (6R,7R)-7-[2-(2-amino-4-thiazolyl)-2-[Z-[(4-t-butoxycarbonyl-2,2-dimethylbenzodioxol-5-yl)methyl]oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]-oct-2-ene-2-carboxylic acid diphenylmethyl ester.

To a suspension of the product obtained in Step 7 (1.2 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (1.8 g) in methylene chloride (45 ml) were added pyridine (0.44 ml) and phosphorous oxychloride (0.27 ml) at $-10°$ C., and the mixture was stirred at $-10°$ C. for 5 hours. To the reaction mixture were added pyridine (0.12 ml) and phosphorous oxychloride (0.07 ml), and the solution was stirred for 1 hour at −10° C. The reaction mixture was then poured into pre-cooled aqueous hydrochloric acid (1N, 300 ml), and extracted once with ethyl acetate (300 ml). The organic layer was washed once with saturated aqueous solution of sodium hydrogen carbonate (300 ml), and once with brine (200 ml), then dried over anhydrous magnesium sulfate. The dried solution was concentrated under reduced pressure. The residue was purified by silica gel column chromatography to give 0.8 g of the objective compound.

IR (KBr; cm$^{-1}$): 1793, 1735, 1719, 1508, 1457, 1247, 1227, 1203.

NMR (DMSO-d$_6$; ppm): 9.7 (1H, d, J=8 Hz), 7.8–6.7 (28H, m), 5.9 (1H, dd, J=8, 5 Hz), 5.24 (1H, d, J=5 Hz), 5.20 (2H, s), 4.3 (2H, s), 3.7 (2H, ABq), 2.5 (3H, s), 1.6 (6H, s), 1.5 (9H, s).

Step 9

Preparation of (6R,7R)-7-[2-(2-amino-4-thiazolyl)-2-[Z-[(2-carboxy-3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a solution of the product of Step 8 (0.8 g) in anisole (0.5 ml) was added trifluoroacetic acid (2 ml) under ice cooling. After stirring at room temperature for 5 hours, the reaction mixture was concentrated under reduced pressure. The residue was then stirred with trifluoroacetic acid (2 ml) for 3 hours. The mixture was poured into ether (100 ml) and the precipitated crystals were collected by filtration. These crystals were suspended in water (6.5 ml) and the pH of the suspension was adjusted to 8.0 with sodium hydrogen carbonate. The resultant solution was applied to a Diaion HP-20 column and eluted with water. Fractions containing the objective compound were collected and concentrated under reduced pressure to ca. 1 ml. The concentrate was crystallized by pouring into ethanol (50 ml) to give 0.22 g of the objective compound.

IR (KBr; cm$^{-1}$): 1762, 1625, 1600, 1509, 1376, 1314.

NMR (D$_2$O; ppm): 7.2 (1H, s), 7.0 (1H, s), 6.9 (2H, s), 5.7 (1H, d, J=5 Hz), 5.5 (2H, s), 5.0 (1H, d, J=5 Hz) 4.4 (2H, ABq), 3.5 (2H, ABq), 2.6 (3H, s).

EXAMPLE 20

Preparation of (6R,7R)-7-[2-(2-amino-4-thiazolyl)-2-[Z-[(2-carboxy-3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

Step 1

Preparation of ethyl 2-(2-amino-4-thiazolyl)-2-[Z-[(4-t-butoxycarbonyl-2,2-dimethylbenzodioxol-5-yl)methyl]oxyimino]acetate.

To a solution of ethyl 2-(2-amino-4-thiazolyl)-2-(Z-hydroxyimino)acetate (1 g) in dry N,N-dimethylformamide (10 ml) was added sodium hydride (60% dispersion in mineral oil; 200 mg) under ice cooling, and the mixture was stirred for 15 minutes. To the mixture was added dropwise a solution of the product obtained Step 4 of Example 19 (1.9 g) in N,N-dimethylformamide (10 ml). The mixture was stirred for 30 minutes under ice cooling then for 2 hours at room temperature. The reaction mixture was then poured into an ice-cooled mixture of conc. hydrochloric acid and ethyl acetate (200 ml each) and stirred vigorously. The organic layer was separated and washed once with saturated aqueous solution of sodium hydrogen carbonate (100 ml) and thrice with brine (100 ml each). The washed solution was dried over anhydrous sodium sulfate. The dried solution was concentrated under reduced pressure, and the residue was crystallized with hexane (50 ml) to give 1.82 g of the objective compound.

NMR (CDCl$_3$; ppm): 6.8 (1H, d, J=8 Hz), 6.7 (1H, d, J=8 Hz), 6.7 (1H, s), 5.7 (2H, brs), 5.4 (2H, s), 4.4 (2H, q, J=7 Hz), 1.7 (6H, s), 1.6 (9H, s), 1.4 (3H, t, J=7 Hz).

Step 2

Preparation 2-(2-amino-4-thiazolyl)-2-[Z-[(4-t-butoxycarbonyl-2,2-dimethylbenzodioxol-5-yl)methyl]oxyimino]acetic acid.

To a suspension of the product of Step 1 (1 g) in ethanol (6 ml) was added an aqueous solution of sodium hydroxide (2N, 2.1 ml), and the mixture was stirred for 1 hour at 65° C. The reaction mixture was concentrated under reduced pressure, and water (20 ml) was added to the residue. The mixture was acidified with aqueous hydrochloric acid (1N) to pH 3, then extracted with ethyl acetate (50 ml). The extracxt was washed twice with brine (30 ml each) and dried over anhydrous sodium sulfate. The dried solution was concentrated under reduced pressure, and the residue was crystallized with ether-hexane (1:1, 30 ml) to give 800 mg of the objective compound.

IR (KBr; cm$^{-1}$): 1717, 1597, 1473, 1456, 1247, 999.

NMR (DMSO-d$_6$; ppm): 7.2 (2H, brs), 6.9 (2H, s), 6.8 (1H, s), 5.2 (2H, s), 1.7 (6H, s), 1.5 (9H, s).

These data are in complete agreement with those of Step 7 of Example 19.

Step 3

Preparation of (6R,7R)-7-[2-(2-amino-4-thiazolyl)-2-[Z-[(2-carboxy-3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The compound of the title given above was prepared from the product of Step 2, according to the methods of Steps 8 and 9 of Example 19.

IR (KBr; cm$^{-1}$): 1762, 1625, 1600, 1509, 1376, 1314.

NMR (D$_2$O; ppm): 7.2 (1H, s), 7.0 (1H, s), 6.9 (2H, s), 5.7 (1H, d, J=5 Hz), 5.5 (2H, ABq), 5.0 (1H, d, J=5 Hz), 4.4 (2H, ABq), 3.5 (2H, ABq), 2.6 (3H, s). These data are in complete agreement with those of Step 9 of Example 19.

According to the method described in Example 19, compounds of Examples 21 and 22, described below, were prepared. According to the method described in Example 20, compounds of Examples 23 and 24, described below, were prepared.

EXAMPLE 21

(6R,7R)-7-[2-(2-amino-4-thiazolyl)-2-[Z-[(2-carboxy-3,4-dihydroxyphenyl)methyl]oxyimino]acetamido]-3-[(5-methyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1763, 1596, 1505, 1380.

NMR (D$_2$O; ppm): 8.5 (1H, s), 7.2 (1H, s), 7.0 (1H, s), 6.9 (2H, s), 5.7 (1H, d, J=5 Hz), 5.5 (2H, ABq), 5.0 (1H, d, J=5 Hz), 4.4 (2H, ABq), 3.5 (2H, ABq), 2.6 (3H, s).

EXAMPLE 22

(6R,7R)-7-[2-(2-amino-4-thiazolyl)-2-[Z-[-(2-carboxy-3,4-dihydroxyphenyl)methyl]oxyimino]acetamido]-3-[(5-carboxy-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1596, 1511, 1372.

NMR (D$_2$O; ppm): 8.5 (1H, s), 7.2 (1H, s), 7.0 (1H, s), 6.9 (2H, s), 5.7 (1H, d, J=5 Hz), 5.5 (2H, ABq), 5.0 (1H, d, J=5 Hz), 4.4 (2H, ABq), 3.5 (2H, ABq).

EXAMPLE 23

(6R,7R)-7-[2-(2-amino-4-thiazolyl)-2-[Z-[(2-carboxy-3,4-dihydroxyphenyl)methyl]oxyimino]acetamido]-3-[(5-carboxymethyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1601, 1505, 1378.

NMR (D$_2$O; ppm): 8.5 (1H, s), 7.2 (1H, s), 7.0 (1H, s), 6.9 (2H, s), 5.7 (1H, d, J=5 Hz), 5.5 (2H, ABq), 5.0 (1H, d, J=5 Hz), 4.4 (2H, ABq), 3.5 (2H, ABq).

EXAMPLE 24

(6R,7R)-7-[2-(2-amino-4-thiazolyl)-2-[Z-[(2-carboxy-3,4-dihydroxyphenyl)methyl]oxyimino]acetamido]-3-[(2-sulfo-5-methyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1763, 1595, 1511, 1375.

NMR (D$_2$O; ppm): 7.2 (1H, s), 7.0 (1H, s), 6.9 (2H, s), 5.7 (1H, d, J=5 Hz), 5.5 (2H, ABq), 5.0 (1H, d, J=5 Hz), 4.4 (2H, ABq), 3.5 (2H, ABq), 2.6 (3H, s).

EXAMPLE 25

Preparation of (6R,7R)-7-[2-(2-amino-4-thiazolyl)-2-[Z-[(3-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 3).

Step 1

Preparation of methyl 2,2,6-trimethylbenzodioxol-4-carboxylate.

To a solution of methyl 2,3-dihydroxy-5-methyl benzoate (33.7 g) in acetone (890 ml) was added phosphorous pentoxide (10 times, 30 g each, interval 30 minutes) with vigorous stirring. After the addition, stirring was continued for further 30 minutes, and the resultant solvent was decanted. The decanted solution was concentrated under reduced pressure. The residue was dissolved in ether (400 ml), washed once with saturated aqueous soltuion of sodium hydrogen carbonate (150 ml), once with brine (150 ml) and dried over anhydrous sodium sulfate. The dried solution was concentrated under reduced pressure. The residue was added to n-hexane (300 ml), and precipitated matter was filtered off. The filtrate was washed thrice with aqueous solution of sodium hydroxide (1N, 100 ml each), once with brine (100 ml) and dried over anhydrous sodium sulfate. The dried solution was concentrated under reduced pressure and the resultant residue was purified by silica gel column chromatography to give 9.8 g of the objective compound.

IR (KBr; cm$^{-1}$): 1720, 1481, 1292, 1254, 1223.

NMR (CDCl$_3$; ppm): 7.1 (1H, s), 6.7 (1H, s), 3.9 (2H, s), 2.3 (3H, s), 1.7 (6H, s).

Step 2

Preparation of 2,2,6-trimethylbenzodioxol-4-carboxylic acid.

To a suspension of the compound (9.5 g) obtained in step 1 in ethanol (100 ml) was added aqueous solution of potassium hydroxide (4N, 20 ml). After refluxing for 25 minutes, the reaction mixture was concentrated under reduced pressure to ca. 30 ml and dissolved in water (150 ml). The solution was washed with ether (50 ml). The aqueous layer was acidified to pH 2 with aqueous hydrochloric acid (4N) and extracted 4 times with ethyl acetate (100 ml each). The combined extracts were washed twice with brine (100 ml each) and dried over anhydrous sodium sulfate. The dried solution was concentrated under reduced pressure. The residue was washed once with n-hexane (100 ml) to give 8.7 g of the objective compound.

IR (KBr; cm$^{-1}$): 1681, 1484, 1307, 1263, 1230.

NMR (DMSO-d$_6$; ppm): 12.7 (1H, brs), 7.0 (1H, d, J=2 Hz), 6.8 (1H, d, J=2 Hz), 2.2 (3H, s), 1.7 (6H, s).

Step 3

Preparation of t-butyl 2,2,6-trimethylbenzodioxol-4-carboxylate

To a suspension of the product obtained in Step 2 (8.5 g) in benzene (70 ml) were added thionyl chloride (11.3 ml) and N,N-dimethylformamide (3 drops). After stirring at 50° for 1 hour, the solvent was removed under reduced pressure. The residue was dissolved in methylene chloride (40 ml), and the solution was added dropwise to an ice-cooled mixture of t-butanol (34.5 ml) and pyridine (18.4 ml). After stirring at room temperature for 39 hours, the solvent was removed under reduced pressure. The residue was dissolved in ether (300 ml), and the ether solution was washed once with water (150 ml), thrice with aqueous hydrochloric acid (1N, 100 ml each), twice with saturated aqueous solution of sodium hydrogen carbonate (100 ml each), once with brine (100 ml) then dried over anhydrous sodium sulfate. The dried solution was concentrated under reduced pressure and the residue was purified by silica gel column chromatography to give 10.1 g of the objective compound.

IR (KBr; cm$^{-1}$): 2977, 1712, 1488, 1300, 1229, 1158, 1081.

NMR (CDCl$_3$; ppm): 7.1 (1H, d, J=2 Hz), 6.7 (1H, d, J=2 Hz), 2.3 (3H, s), 1.7 (6H, s), 1.6 (9H, s).

Step 4

Preparation of t-butyl 6-bromomethyl-2,2-dimethylbenzodioxol-4-carboxylate.

To a solution of the product obtained in Step 3 (10 g) in carbon tetrachloride (60 ml) were added N-bromosuccinimide (6.75 g) and benzoyl peroxide (30 mg), and the mixture was refluxed for 30 minutes. The reaction mixture was then cooled to room temperature and insoluble matter was removed by filtraton. The filtrate was washed once each with water (50 ml) and brine (50 ml), then concentrated under reduced pressure. The residue was purified by silica gel column chromatography to give 12.9 g of the objective compound.

IR (KBr; cm$^{-1}$): 1722, 1477, 1306, 1265, 1232, 1153, 1081, 1017.

NMR (CDCl$_3$; ppm): 7.3 (1H, d, J=2 Hz), 6.9 (1H, d, J=2 Hz) 4.4 (2H, s), 1.7 (6H, s), 1.6 (9H, s).

Step 5

Preparation of t-butyl 2,2-dimethyl-6-(N-phthaloyloxymethyl)benzodioxol-4-carboxylate.

To a solution of the product obtained in Step 4 (12.9 g) in acetonitrile (35 ml) were added dropwise a solution of N-hydroxyphthalimide (6.17 g) and a solution of triethylamine (5.3 ml) in acetonitrile (35 ml) at room temperature. After stirring for 3 hours, the reaction mixture was concentrated to about 40 ml, poured into ice water (300 ml), then extracted twice with ethyl acetate (200 ml and 100 ml). The organic layer was washed twice with aqueous solution of citric acid (1N, 150 ml each), four times with saturated aqueous solution of sodium hydrogen carbonate (100 ml each) and once with brine (100 ml). The washed solution was dried over anhydrous sodium sulfate. The dried solution was concentrated under reduced pressure, and the residue was crystallized with n-hexane (150 ml) to give 12.3 g of the objective compound.

IR (KBr; cm$^{-1}$): 1733, 1719, 1378, 1305, 1263, 1164, 975.

NMR (CDCl$_3$; ppm): 7.8 (4H, m), 7.4 (1H, d, J=2 Hz), 7.1 (1H, d, J=2 Hz), 5.1 (2H, s), 1.7 (6H, s), 1.6 (9H, s).

Step 6

Preparation of t-butyl 6-aminooxymethyl-2,2-dimethylbenzodioxol-4-carboxylate.

To a solution of the product obtained in Step 5 (12.2 g) in methylene chloride (180 ml) was added a solution of methylhydrazine (1.67 ml) in methylene chloride (20 ml) at −30° C. After stirring for 1 hour under ice cooling, methylhydrazine (0.15 ml) was added and the reaction mixture was stirred further 30 minutes under ice cooling. Insoluble matter was filtered off, and the filtrate was concentrated under reduced pressure. The residue was purified by silica gel column chromatography to give 8.3 g of the objective compound.

IR (neat; cm$^{-1}$): 1715, 1482, 1305, 1264, 1231, 1155, 1080.

NMR (CDCl$_3$; ppm):

7.3 (1H, s), 6.9 (1H, s), 5.5 (2H, brs), 4.7 (2H, s) 1.7 (6H, s), 1.6 (9H, s).

Step 7

Preparation 2-(2-amino-4-thiazolyl)-2-[Z-[(4-t-butoxycarbonyl-2,2-dimethylbenzodioxol-6-yl)methyl]oxyimino]acetic acid.

To a solution of the product obtained in Step 6 (8.1 g) in N,N-dimethylformamide (35 ml) was added (2-aminothiazol-4-yl)glyoxylic acid (4.7 g), and the mixture was stirred at room temperature for 60 minutes. The reaction mixture was poured into ice-water (400 ml), and precipitated crystals were collected by filtration. The crystals were dissolved in ethyl acetate (500 ml) and washed twice with water (150 ml each), twice with brine (150 ml each) and dried over anhydrous sodium sulfate. After filtrating drying agent, the filtrate was concentrated under reduced pressure and the residue was crystallized with ether (100 ml) to give 9.3 g of the objective compound.

IR (neat; cm$^{-1}$): 1708, 1636, 1480, 1263, 1154.

NMR (DMSO-d$_6$; ppm): 7.2 (2H, brs), 7.2 (1H, d, J=2 Hz), 7.0 (1H, d, J=2 Hz), 6.8 (1H, s), 5.0 (2H, s), 1.7 (6H, s) 1.5 (9H, s).

Step 8

Preparation of (6R,7R)-7-[2-(2-amino-4-thiazolyl)-2-[Z-[(4-t-butoxycarbonyl-2,2-dimethylbenzodioxol-6-yl)methyl]oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]-oct-2-ene-2-carboxylic acid diphenylmethyl ester.

To a suspension of the product obtained in Step 7 (0.98 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (1.5 g) in methylene chloride (20 ml) were added pyridine (0.35 ml) and a solution of phosphorous oxychloride (0.10 ml) in methylene chloride (1 ml) at −10° C., and the mixture was stirred at −10° C. for 1 hour. To the solution were added pyridine (0.17 ml) and phosphorous oxychloride (0.1 ml), and the mixture was stirred for further 1 hour at −10° C. The reaction mixture was then poured into pre-cooled aqueous hydrochloric acid (1N, 100 ml), and extracted once with ethyl acetate (500 ml). The organic layer was washed once with aqueous hydrochloric acid (1N, 100 ml), twice with saturated aqueous solution of sodium hydrogen carbonate (100 ml each), twice with brine (100 ml each) then dried over anhydrous sodium sulfate. The dried solution was concentrated under reduced pressure and the residue was purified by silica gel column chromatography to give 1.0 g of the objective compound.

IR (KBr; cm$^{-1}$): 1791, 1735, 1718, 1508, 1377, 1304, 1261, 1226, 1204, 1183, 1154.

NMR (DMSO-d$_6$; ppm): 9.7 (1H, d, J=8 Hz), 7.6–6.9 (27H, m), 6.7 (1H, s), 5.9 (1H, dd, J=8, 5 Hz), 5.3 (1H, d, J=5 Hz), 5.0 (2H, s), 4.3 (2H, s), 3.7 (2H, ABq), 2.6 (3H, s), 1.6 (6H, s), 1.5 (9H, s).

Step 9

Preparation of (6R,7R)-7-[2-(2-amino-4-thiazolyl)-2-[Z-[(3-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To an ice-cooled solution of anisole (0.7 ml) in trifluoroacetic acid (2.5 ml) was added the product obtained in step 8 (0.97 g). After stirring at room temperature for 7 hours, trifluoroacetic acid (0.5 ml) was added to the reaction mixture and stirring was continued for further 30 minutes, and poured into ether (100 ml). The precipitated crystals were collected by filtration and suspended in water (8 ml). The pH of the suspension was adjusted to 8.0 with sodium hydrogen carbonate. The resultant solution was applied to a Diaion HP-20 column and eluted with water. Fractions containing objective compound were collected and concentrated under reduced pressure to ca. 1 ml. The concentrate was crystallized by pouring into ethanol (30 ml) to give 0.48 g of the objective compound.

IR (KBr; cm$^{-1}$): 1762, 1598, 1509, 1405, 1314.

NMR (D$_2$O; ppm): 7.4 (1H, d, J=2 Hz), 7.2 (1H, s), 7.1 (1H, d, J=2 Hz), 7.0 (1H, s), 5.7 (1H, d, J=5 Hz), 5.1 (2H, s), 5.0 (1H, d, J=5 Hz), 4.3 (2H, ABq), 3.5 (2H, ABq), 2.6 (3H, s).

EXAMPLE 26

Preparation of (6R,7R)-7-[2-(2-amino-4-thiazolyl)-2-[Z-[(3-carboxy-4,5-dihydroxyphenyl)methyl]oxyimino]acetamido]-3-[(2-carboxy-5-methyl-s- triazolo[1,5-a]pyrimidin-7-yl)thiomethyl]-8-oxo-5-thia-1-azabicyclo[4.2.0]oct-2-ene-2-carboxylic acid.

Step 1

Preparation of ethyl 2-(2-amino-4-thiazolyl)-2-[Z-[(4-t-butoxycarbonyl-2,2-dimethylbenzodioxol-6-yl)methyl]oxyimino]acetate.

To a solution of ethyl 2-(2-amino-4-thiazolyl)-2-(Z-hydroxyimino)acetate (1 g) in dry N,N-dimethylformamide (10 ml) was added 60% sodium hydride (200 mg) under ice cooling, and the mixture was stirred for 15 minutes. To the mixture was added dropwise a solution of the product obtained in Step 4 of Example 1 (1.9 g) in N,N-dimethylformamide (10 ml). After stirring for 30 minutes under ice cooling, the mixture was stirred at room temperature for 1.5 hour. The reaction mixture was then poured into an ice-cooled mixture of conc. hydrochloric acid and ethyl acetate (200 ml each) and stirred thoroughly. The organic layer was separated and washed once with saturated aqueous solution of sodium hydrogen carbonate (100 ml) and thrice with brine (100 ml each). The washed solution was dried over anhydrous sodium sulfate. The dried solution was concentrated under reduced pressure, and the residue was crystallized with hexane (50 ml) to give 1.90 g of the objective compound.

NMR (CDCl$_3$; ppm): 7.3 (1H, d, J=2 Hz), 6.9 (1H, d, J=2 Hz), 6.7 (1H, s), 5.7 (2H, brs), 5.2 (2H, s), 4.4 (2H, q, J=7 Hz), 1.7 (6H, s), 1.6 (9H, s), 1.4 (3H, t, J=7 Hz).

Step 2

Preparation 2-(2-amino-4-thiazolyl)-2-[Z-[(4-t-butoxycarbonyl-2,2-dimethylbenzodioxol-6-yl)methyl]oxyimino]acetic acid.

To a suspension of the product of Step 1 (1 g) in methanol (6 ml) was added an aqueous solution of sodium hydroxide (2N, 2.1 ml), and the mixture was stirred for 1 hour at 65° C. The reaction mixture was concentrated under reduced pressure, and water (20 ml) was added to the residue. The mixture was acidified with aqueous hydrochloric acid (1N) to pH 3, then extracted with ethyl acetate (50 ml). The extract was washed twice with brine (30 ml each) and dried over anhydrous sodium sulfate. The dried solution was concentrated under reduced pressure, and the residue was crystallized with ether-hexane (1:1, 30 ml) to give 840 mg of the objective compound.

IR (KBr; cm$^{-1}$): 1708, 1636, 1480, 1263, 1154.

NMR (DMSO-d$_6$; ppm): 7.2 (2H, brs), 7.2 (1H, d, J=2 Hz), 7.0 (1H, d, J=2 Hz), 6.8 (1H, s), 5.0 (2H, s), 1.7 (6H, s), 1.5 (9H, s).

These data are in complete agreement with those of Step 7 of Example 25.

Step 3

Preparation of (6R,7R)-7-[2-(2-amino-4-thiazolyl)-2-[Z-[(3-carboxy-4,5-dihydroxyphenyl)methyl]oxyimino]acetamido]-3-[(2-carboxy-5-methyl-s-triazolo[1,5-a]pyrimidin-7yl)thiomethyl]-8-oxo-5-thia-1-azabicyclo[4.2.0]oct-2-ene-2-carboxylic acid.

The compound of the title given above was prepared from the product of Step 2, according to the methods of Steps 8 and 9 of Example 25.

IR (KBr; cm$^{-1}$): 1762, 1598, 1509, 1405, 1314.

NMR (D$_2$O; ppm): 7.4 (1H, d, J=2 Hz), 7.2 (1H, s), 7.1 (1H, d, J=2 Hz), 7.0 (1H, s), 5.7 (1H, d, J=5 Hz), 5.1 (2H, s), 5.0 (1H, d, J=5 Hz), 4.3 (2H, ABq) 3.5 (2H, ABq), 2.6 (3H, s). These data are in complete agreement with those of Step 9 of Example 25.

According to the method described in Example 25, compounds of Examples 27 and 28, described below, were prepared. According to the method described in Example 26, compounds of Examples 29 and 30, described below, were prepared.

EXAMPLE 27

(6R,7R)-7-[2-(2-amino-4-thiazolyl)-2-[Z-[(3-carboxy-4,5-dihydroxyphenyl)methyl]oxyimino]acetamido]-3-[(5-methyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1596, 1510, 1401.

NMR (D$_2$O; ppm): 8.5 (1H, s), 7.4 (1H, d, J=2 Hz), 7.2 (1H, s), 7.1 (1H, d, J=2 Hz), 7.0 (1H, s), 5.7 (1H, d, J=5 Hz), 5.1 (2H, s), 5.0 (1H,d, J=5 Hz), 4.3 (2H, ABq), 3.5 (2H, ABq), 2.6 (3H, s).

EXAMPLE 28

(6R,7R)-7-[2-(2-amino-4-thiazolyl)-2-[Z-[-(3-carboxy-4,5-dihydroxyphenyl)methyl]oxyimino]acetamido]-3-[(5-carboxy-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1598, 1515, 1398.

NMR (D$_2$O; ppm): 8.5 (1H, s), 7.4 (1H, d, J=2 Hz), 7.2 (1H, s), 7.1 (1H, d, J=2Hz), 7.0 (1H, s), 5.7 (1H, d, J=5 Hz), 5.1 (2H, s), 5.0 (1H, d, J=5 Hz), 4.3 (2H, ABq), 3.5 (2H, ABq).

EXAMPLE 29

(6R,7R)-7-[2-(2-amino-4-thiazolyl)-2-[Z-[(3-carboxy-4,5-dihydroxyphenyl)methyl]oxyimino]acetamido]-3-[(5-carboxymethyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1763, 1595, 1515, 1398.

NMR (D$_2$O; ppm): 8.5 (1H, s), 7.4 (1H, d, J=2 Hz), 7.2 (1H, s), 7.1 (1H, d, J=2 Hz), 7.0 (1H, s), 5.7 (1H, d, J=5 Hz), 5.1 (2H, s), 5.0 (1H, d, J=5 Hz), 4.3 (2H, ABq), 3.5 (2H, ABq), 2.6 (2H,s).

EXAMPLE 30

(6R,7R)-7-[2-(2-amino-4-thiazolyl)-2-[Z-[(3-carboxy-4,5-dihydroxyphenyl)methyl]oxyiminoacetamido]-3-[(2-sulfo-5-methyl-s-triazolo[1,5-a]pyrimidin-7-yl)thiomethyl]-8-oxo-5-thia-1-azabicyclo[4.2.0]oct-2-ene-2-carboxylic acid IR (KBr; cm$^{-1}$): 1762, 1597, 1512, 1400.

NMR (D$_2$O; ppm): 7.4 (1H, d, J=2 Hz), 7.2 (1H, s), 7.1 (1H, d, J=2 Hz), 7.0 (1H, s), 5.7 (1H, d, J=5 Hz), 5.1 (2H, s), 5.0 (1H, d, J=5 Hz), 4.3 (2H, ABq), 3.5 (2H, ABq), 2.6 (3H, s).

The following examples detail typical pharmaceutical preparations containing the cephalosporin derivatives of the present invention. These examples are not intended to limit the types of compounds to be used, but the methods are applicable to all the compounds of the present invention.

EXAMPLE A (Method of manufacturing freeze-dried parenteral injections)

(6R,7R)-7-[2-(2-amino-4-thiazolyl)-2-[Z-[(5-carboxy-2,3-dihydroxyphenlyl)methyl]oxyimino]acetamido]-

3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid trisodium salt (500 g) was dissolved in 2.0 l of sterile water and 2 ml each of this solution was poured into 10-ml ampoules, freeze-dried and sealed by ordinary methods, to produce a freeze-dried preparation for parenteral injections.

EXAMPLE B (Method of manufacturing tablets for oral administration)

Granules were prepared by ordinary methods using 100 g of (6R,7R)-7-[2-(2-amino-4-thiazolyl)-2-[Z-[(6-carboxy-2,3-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid, 100 g of lactose, 30 g of starch, and 10 g of polyvinyl pyrrolidone. Starch (30 g) and magnesium stearate (5 g) were further added to the granules, and the resulting mixture was compressed into tablets, each piece weighing 275 mg.

EXAMPLE C (Method of manufacturing gelatin capsules for oral administration)

(6R,7R)-7-[2-(2-amino-4-thiazolyl)-2-[Z-[(3-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (100 g), water-soluble polyvinyl pyrrolidone (15 g), mannitol (15 g), talc (15 g) and magnesium stearate (5 g) were uniformly mixed, and filled into gelatin capsules each weighing 150 mg.

What is claimed is:

1. A cephalosporin compound of the formula (I):

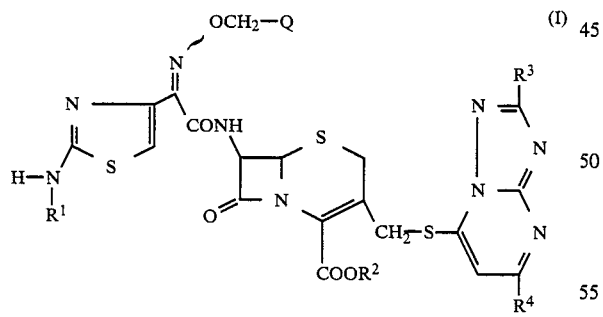

and non-toxic salts, non-toxic solvates and non-toxic salts of solvates thereof; wherein $R^1$ represents a hydrogen atom or an amino-protecting group, $R^2$ represents a hydrogen atom or a carboxy-protecting group, $R^3$ represents a hydrogen atom, a hydroxy group, an amino group, a sulfo group, a carboxy group or a protected carboxy group, $R^4$ represents a hydrogen atom, a methyl group, a carboxy group, a protected carboxy group, a carboxymethyl group or a protected carboxymethyl group, Q represents a group:

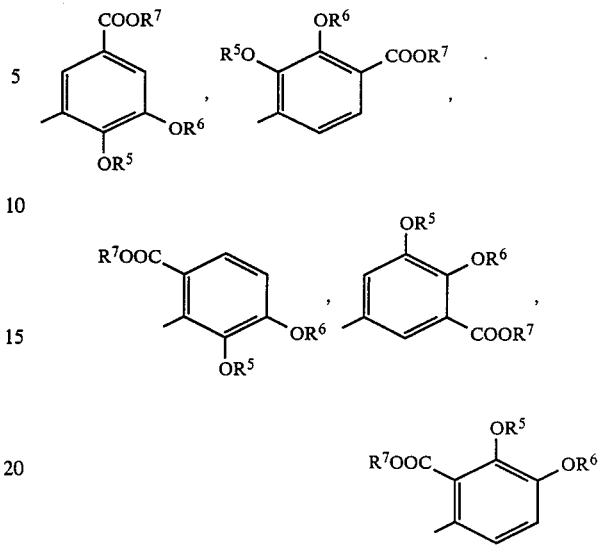

wherein $R^5$ and $R^6$ are same or different and represent hydrogen atom, hydroxy-protecting group or together a vicinal diol protecting group, and $R^7$ represents a hydrogen atom or carboxy-protecting group, and the bond shown with a wavy line represents a bond of anti-form or syn-form.

2. A cephalosporin compound as claimed in claim 1 wherein $R^3$ represents a carboxy group or a protected carboxy group, and $R^4$ represents a methyl group.

3. A cephalosporin compound as claimed in claim 2 wherein Q represents a group:

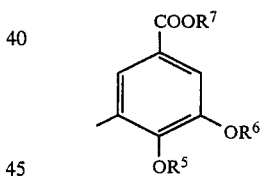

wherein $R^5$ and $R^6$ are same or different and represent hydrogen atoms, hydroxy-protecting groups or together a vicinal diol protecting group, $R^7$ represents a hydrogen atom or a carboxy-protecting group.

4. A cephalosporin compound as claimed in claim 2 wherein Q represents a group:

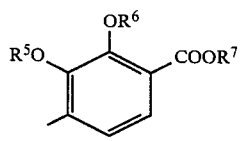

wherein $R^5$ and $R^6$ are same or different and represent hydrogen atoms, hydroxy-protecting groups or together a vicinal diol protecting group, $R^7$ represents a hydrogen atom or a carboxy-protecting group.

5. A cephalosporin compound as claimed in claim 2 wherein Q represents a group:

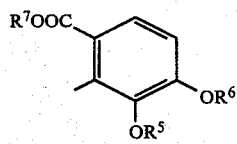

wherein $R^5$ and $R^6$ are same or different and represent hydrogen atoms, hydroxy-protecting groups or together a vicinal diol protecting group, $R^7$ represents a hydrogen atom or a carboxy-protecting group.

6. A cephalosporin compound as claimed in claim 2 wherein Q represents a group:

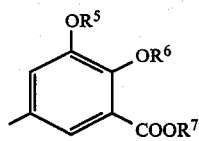

wherein $R^5$ and $R^6$ are same or different and represent hydrogen atoms, hydroxy-protecting groups or together a vicinal diol protecting group, $R^7$ represents a hydrogen atom or a carboxy-protecting group.

7. A cephalosporin compound as claimed in claim 2 wherein Q represents a group:

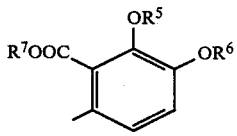

wherein $R^5$ and $R^6$ are same or different and represent hydrogen atoms, hydroxy-protecting groups or together a vicinal diol protecting group, $R^7$ represents a hydrogen atom or a carboxy-protecting group.

8. A cephalosporin compounds as claimed in claim 1 wherein the said bond shown with a wavy line represents a bond of syn-form.

9. An antibiotic pharmaceutical composition which comprises an effective amount of one or more cephalosporin compounds represented by the formula: (I):

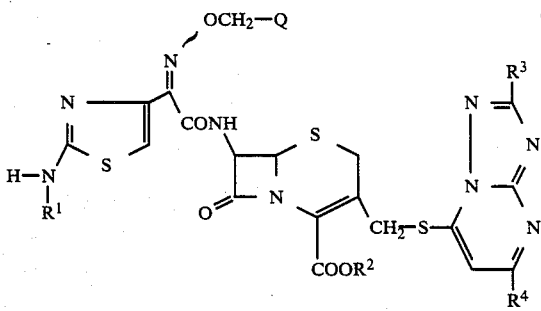

and non-toxic salts, non-toxic solvates and non-toxic salts of solvates thereof and a pharmaceutically acceptable carrier; wherein $R^1$ represents a hydrogen atom or an amino-protecting group, $R^2$ a hydrogen atom or carboxy-protecting groups, $R^3$ represents a hydrogen atom, a hydroxy group, an amino group, a sulfo group, a carboxy group or a protected carboxy group, $R^4$ represents a hydrogen atom, a methyl group, a carboxy group, a protected carboxy group, Q represents a group

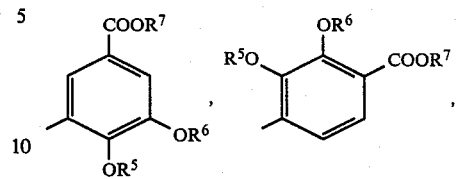

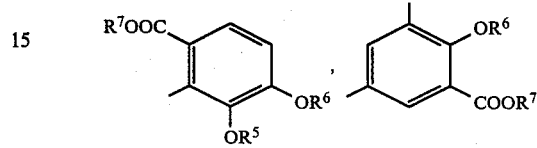

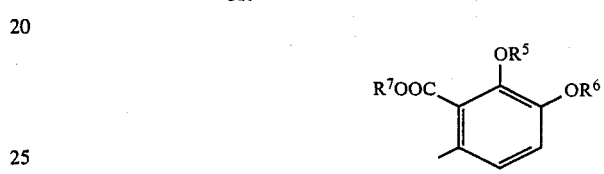

wherein $R^5$ and $R^6$ are same or different and represent hydrogen atoms, hydroxy-protecting groups or together a vicinal diol protecting group, $R^7$ represents a hydrogen atom or carboxy-protecting group, and the bond shown with a wavy line represents a bond of anti-form or syn-form.

10. The antibiotic pharmaceutical composition of claim 9 wherein Q represents a group:

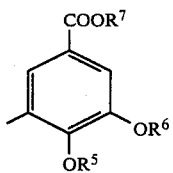

wherein $R^5$ and $R^6$ are same or different and represent a hydrogen atoms, hydroxy-protecting groups or together a vicinal diol protecting group, $R^7$ represents a hydrogen atom or carboxy-protecting group.

11. The antibiotic pharmaceutical composition of claim 9 wherein Q represents a group:

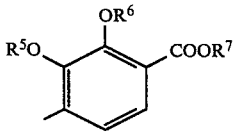

wherein $R^5$ and $R^6$ are same or different and represent a hydrogen atoms, hydroxy-protecting groups or together a vicinal diol protecting group, $R^7$ represents a hydrogen atom or carboxy-protecting group.

12. The antibiotic pharmaceutical composition of claim 9 wherein Q represents a group:

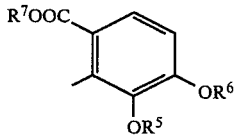

wherein $R^5$ and $R^6$ are same or different and represent a hydrogen atoms, hydroxy-protecting groups or together a vicinal diol protecting group, $R^7$ represents a hydrogen atom or carboxy-protecting group.

13. The antibiotic pharmaceutical composition of claim 9 wherein Q represents a group:

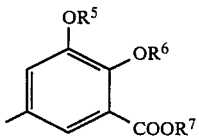

wherein $R^5$ and $R^6$ are same or different and represent a hydrogen atoms, hydroxy-protecting groups or together a vicinal diol protecting group, $R^7$ represents a hydrogen atom or carboxy-protecting group.

14. The antibiotic pharmaceutical composition of claim 9 wherein Q represents a group:

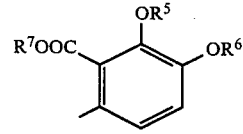

wherein $R^5$ and $R^6$ are same or different and represent a hydrogen atoms, hydroxy-protecting groups or together a vicinal diol protecting group, $R^7$ represents a hydrogen atom or carboxy-protecting group.

15. The antibiotic pharmaceutical composition of claim 9 wherein the said bond shown with a wavy line represents a bond of syn-form.

* * * * *